(12) United States Patent
Lorsch

(10) Patent No.: US 9,767,254 B2
(45) Date of Patent: Sep. 19, 2017

(54) PREPAID CARD FOR SERVICES RELATED TO PERSONAL HEALTH RECORDS

(71) Applicant: MyMedicalRecords, Inc., Los Angeles, CA (US)

(72) Inventor: Robert H. Lorsch, Los Angeles, CA (US)

(73) Assignee: MYMEDICALRECORDS, INC., Los Angeles, CA (US)

( * ) Notice: Subject to any disclaimer, the term of this patent is extended or adjusted under 35 U.S.C. 154(b) by 0 days.

(21) Appl. No.: 13/736,340

(22) Filed: Jan. 8, 2013

(65) Prior Publication Data

US 2013/0179194 A1     Jul. 11, 2013

Related U.S. Application Data

(60) Provisional application No. 61/584,599, filed on Jan. 9, 2012, provisional application No. 61/600,859, filed on Feb. 20, 2012.

(51) Int. Cl.
*G06F 19/00* (2011.01)
*G06Q 20/34* (2012.01)
(Continued)

(52) U.S. Cl.
CPC .......... *G06F 19/323* (2013.01); *G06F 19/322* (2013.01); *G06Q 20/28* (2013.01);
(Continued)

(58) Field of Classification Search
CPC ......... G06Q 50/22; G06Q 50/24; G06Q 30/06
See application file for complete search history.

(56) References Cited

U.S. PATENT DOCUMENTS 5,404,292 A   4/1995   Hendrickson
5,494,292 A   2/1996   Mileti
(Continued)

FOREIGN PATENT DOCUMENTS

EP   0764911       3/1997
EP   0764911 A1    3/1997
(Continued)

OTHER PUBLICATIONS

Heart Record Registration, http://web.archive.org/web/20010424161606/http://www.heartcenteronline.com/myheartdr/patientrecord/register.cfm, 2 pags. Nov. 7, 2013.
(Continued)

*Primary Examiner* — Robert Sorey
*Assistant Examiner* — Kristine Rapillo
(74) *Attorney, Agent, or Firm* — Goodhue, Coleman & Owens, P.C.

(57) ABSTRACT

A prepaid card allows for prepaying for access to a web site configured to provide for management of personal health care records. The prepaid card includes a first surface, a second surface opposite the first surface, a promotional code printed on the second surface, a scratch box on the second surface and overlaying the promotional code. The promotional code may be associated with a monetary value for the prepaid card on the web site configured to provide for management of personal health care records. A method for providing a service facilitating online management of personal health records includes receiving data from a prepaid card at a web server, activating a new user account for the online management of personal health records using the data from the prepaid card; and providing online access to the new user account.

12 Claims, 32 Drawing Sheets

(51) Int. Cl.
*G06Q 20/28* (2012.01)
*G06Q 50/24* (2012.01)

(52) U.S. Cl.
CPC .......... *G06Q 20/34* (2013.01); *G06Q 20/342* (2013.01); *G06Q 50/24* (2013.01)

(56) References Cited

U.S. PATENT DOCUMENTS

| | | |
|---|---|---|
| 5,499,293 A | 3/1996 | Behram et al. |
| 5,597,995 A | 1/1997 | Williams et al. |
| 5,619,991 A | 4/1997 | Sloane |
| 5,737,539 A | 4/1998 | Edelson et al. |
| 5,758,095 A | 5/1998 | Albaum et al. |
| 5,778,882 A | 7/1998 | Raymond et al. |
| 5,790,785 A | 8/1998 | Klug et al. |
| 5,797,515 A | 8/1998 | Liff et al. |
| 5,801,755 A | 9/1998 | Echerer |
| 5,832,488 A | 11/1998 | Eberhardt |
| 5,903,633 A | 5/1999 | Lorsch |
| 5,918,909 A | 7/1999 | Fiala et al. |
| 5,924,074 A | 7/1999 | Evans |
| 5,926,526 A | 7/1999 | Rapaport et al. |
| 5,930,759 A | 7/1999 | Moore et al. |
| 5,970,463 A | 10/1999 | Cave et al. |
| 5,974,124 A | 10/1999 | Schlueter, Jr. et al. |
| 5,997,476 A | 12/1999 | Brown |
| 6,000,828 A | 12/1999 | Leet |
| 6,032,119 A | 2/2000 | Brown et al. |
| 6,073,106 A | 6/2000 | Rozen et al. |
| 6,082,776 A | 7/2000 | Feinberg |
| 6,088,677 A | 7/2000 | Spurgeon |
| 6,192,113 B1 | 2/2001 | Lorsch |
| 6,223,559 B1 | 5/2001 | Coleman |
| 6,463,417 B1 | 10/2002 | Schoenberg |
| 6,493,427 B1 | 12/2002 | Kobylevsky et al. |
| 6,523,009 B1 | 2/2003 | Wilkins |
| 6,574,484 B1 | 6/2003 | Carley |
| 6,640,974 B2 * | 11/2003 | Malone ................ A45C 11/182 206/449 |
| 6,651,060 B1 | 11/2003 | Harper et al. |
| 6,654,724 B1 | 11/2003 | Rubin et al. |
| 6,725,200 B1 | 4/2004 | Rost |
| 6,738,784 B1 | 5/2004 | Howes |
| 6,845,448 B1 | 1/2005 | Chaganti et al. |
| 6,871,214 B2 | 3/2005 | Parsons et al. |
| 6,874,085 B1 | 3/2005 | Koo et al. |
| 6,941,271 B1 | 9/2005 | Soong |
| 6,954,802 B2 | 10/2005 | Sutherland et al. |
| 6,988,075 B1 | 1/2006 | Hacker |
| 7,028,049 B1 | 4/2006 | Shelton |
| 7,257,967 B2 | 8/2007 | Rheinstein |
| 7,287,031 B1 | 10/2007 | Karpf et al. |
| 7,306,560 B2 | 12/2007 | Iliff |
| 7,428,494 B2 | 9/2008 | Hasan et al. |
| 7,440,904 B2 | 10/2008 | Hasan et al. |
| 7,475,020 B2 | 1/2009 | Hasan et al. |
| 7,509,264 B2 | 3/2009 | Hasan et al. |
| 7,533,030 B2 | 5/2009 | Hasan et al. |
| 7,587,368 B2 | 9/2009 | Felsher |
| 7,613,620 B2 | 11/2009 | Salwan |
| 7,630,986 B1 | 12/2009 | Herz et al. |
| 7,661,146 B2 | 2/2010 | Karimzadeh et al. |
| 7,685,003 B2 | 3/2010 | Hasan et al. |
| 7,693,730 B2 | 4/2010 | Hasan et al. |
| 7,707,047 B2 | 4/2010 | Hasan et al. |
| 7,720,691 B2 | 5/2010 | Hasan et al. |
| 7,769,601 B1 | 8/2010 | Bleser et al. |
| 7,827,043 B2 | 11/2010 | Tahan |
| 7,865,373 B2 | 1/2011 | Punzak et al. |
| 7,949,545 B1 | 5/2011 | Madras et al. |
| 7,996,244 B1 | 8/2011 | Fitch |
| 8,010,717 B2 | 8/2011 | Evans et al. |
| 8,024,273 B2 | 9/2011 | Deobhakta et al. |
| 8,041,749 B2 | 10/2011 | Beck |
| 8,073,710 B2 | 12/2011 | Hasan et al. |
| 8,090,590 B2 | 1/2012 | Fotsch et al. |
| 8,108,311 B2 | 1/2012 | Herlitz |
| 8,117,045 B2 | 2/2012 | Lorsch |
| 8,117,646 B2 | 2/2012 | Lorsch |
| 8,121,855 B2 | 2/2012 | Lorsch |
| 8,131,563 B2 | 3/2012 | Hasan et al. |
| 8,135,596 B2 | 3/2012 | Jung et al. |
| 8,165,896 B2 | 4/2012 | Jung et al. |
| 8,180,654 B2 | 5/2012 | Berkman et al. |
| 8,214,234 B2 | 7/2012 | Hasan et al. |
| 8,301,466 B2 | 10/2012 | Lorsch |
| 8,321,240 B2 | 11/2012 | Lorsch |
| 8,352,287 B2 | 1/2013 | Lorsch |
| 8,352,288 B2 | 1/2013 | Lorsch |
| 2001/0034615 A1 | 10/2001 | Wilkinson et al. |
| 2001/0039503 A1 | 11/2001 | Chan et al. |
| 2001/0041991 A1 | 11/2001 | Segal et al. |
| 2001/0056359 A1 | 12/2001 | Abreu |
| 2002/0004727 A1 | 1/2002 | Knaus et al. |
| 2002/0016718 A1 | 2/2002 | Rothschild et al. |
| 2002/0026332 A1 | 2/2002 | Snowden et al. |
| 2002/0029157 A1 | 3/2002 | Marchosky |
| 2002/0046061 A1 | 4/2002 | Wright et al. |
| 2002/0059587 A1 | 5/2002 | Cofano et al. |
| 2002/0077861 A1 | 6/2002 | Hogan |
| 2002/0091573 A1 | 7/2002 | Hodes |
| 2002/0103675 A1 | 8/2002 | Vanelli |
| 2002/0111946 A1 | 8/2002 | Fallon |
| 2002/0120470 A1 | 8/2002 | Trice, Sr. |
| 2002/0128865 A1 | 9/2002 | Alten |
| 2002/0138302 A1 | 9/2002 | Bodnick |
| 2002/0138306 A1 | 9/2002 | Sabovich |
| 2002/0178631 A1 | 12/2002 | Morton |
| 2002/0189146 A1 | 12/2002 | Lyon |
| 2002/0194024 A1 | 12/2002 | Kleinschmidt |
| 2003/0004889 A1 | 1/2003 | Fiala et al. |
| 2003/0014282 A1 | 1/2003 | Haaksma et al. |
| 2003/0037065 A1 | 2/2003 | Svab |
| 2003/0040940 A1 | 2/2003 | Nehammer |
| 2003/0055824 A1 | 3/2003 | Califano |
| 2003/0059751 A1 | 3/2003 | Welles |
| 2003/0086591 A1 | 5/2003 | Simon |
| 2003/0098356 A1 | 5/2003 | Gombar |
| 2003/0132132 A1 | 7/2003 | Small |
| 2003/0140044 A1 | 7/2003 | Mok et al. |
| 2003/0154411 A1 | 8/2003 | Hovik |
| 2003/0200179 A1 * | 10/2003 | Kwan ................... G06Q 20/04 705/65 |
| 2003/0208382 A1 | 11/2003 | Westfall |
| 2003/0220822 A1 | 11/2003 | Fiala et al. |
| 2003/0226889 A1 | 12/2003 | Morrison, Jr. |
| 2003/0229452 A1 | 12/2003 | Lewis et al. |
| 2003/0233257 A1 | 12/2003 | Matian et al. |
| 2003/0233844 A1 | 12/2003 | Rheinstein |
| 2004/0019794 A1 | 1/2004 | Moradi et al. |
| 2004/0078229 A1 | 4/2004 | Gay et al. |
| 2004/0139318 A1 | 7/2004 | Fiala et al. |
| 2004/0162895 A1 | 8/2004 | Mok et al. |
| 2004/0172295 A1 | 9/2004 | Dahlin et al. |
| 2004/0172307 A1 | 9/2004 | Gruber |
| 2004/0186746 A1 | 9/2004 | Angst et al. |
| 2004/0199765 A1 | 10/2004 | Kohane et al. |
| 2004/0228336 A1 | 11/2004 | Kung et al. |
| 2004/0267572 A1 | 12/2004 | Emery et al. |
| 2005/0075909 A1 | 4/2005 | Flagstad |
| 2005/0154614 A1 | 7/2005 | Swanson et al. |
| 2005/0165285 A1 | 7/2005 | Iliff |
| 2005/0165627 A1 | 7/2005 | Fotsch et al. |
| 2005/0209891 A1 | 9/2005 | Jacobus et al. |
| 2005/0251423 A1 | 11/2005 | Bellam et al. |
| 2006/0004588 A1 | 1/2006 | Ananda |
| 2006/0064320 A1 | 3/2006 | Postrel |
| 2006/0229909 A1 | 10/2006 | Kaila et al. |
| 2007/0061169 A1 | 3/2007 | Lorsch |
| 2007/0061170 A1 | 3/2007 | Lorsch |
| 2007/0078677 A1 | 4/2007 | Hofstetter |
| 2007/0233519 A1 * | 10/2007 | Lorsch ................. G06F 19/322 705/3 |
| 2008/0177669 A1 | 7/2008 | Marshall |

(56) References Cited

U.S. PATENT DOCUMENTS

| | | | |
|---|---|---|---|
| 2008/0183504 | A1 | 7/2008 | Highley |
| 2009/0007237 | A1 | 1/2009 | Lorsch |
| 2009/0055222 | A1 | 2/2009 | Lorsch |
| 2011/0112919 | A1* | 5/2011 | Gray ..................... G06Q 20/12 705/17 |
| 2011/0276437 | A1* | 11/2011 | Mullen ............ G06K 19/06206 705/27.1 |

FOREIGN PATENT DOCUMENTS

| | | |
|---|---|---|
| JP | 9218902 | 8/1997 |
| JP | 2001350847 | 12/2001 |
| WO | 0227999 | 4/2002 |

OTHER PUBLICATIONS

For Physicians, http://web.archive.org/web/20050524080851/http://www.ihealthrecord.org/forPhysicians.html, 2 pages. Nov. 7, 2013.

iHEALTHRECORD FAQs, https://web.archive.org/web/20050525032329/http://www.ihealthrecord.org/faq.html, 2 pages. Nov. 7, 2013.

medicarecord.com, https://webarchive.org/web/19991012053847/http://medicalrecord.com/, 2 pages. Nov. 5, 2013.

medicalrecord.com, https://web.archive.org/web/19991012063749/http://medicalrecord.com/press.asp, 5 pages. Nov. 4, 2013.

Help Center, https://web.archive.org/web/20040404033910/http://personalmd.com/help/efile.shtml, 2 pages. Nov. 7, 2013.

Synchart, https://web.archive.org/web/20040614051913/http://www.synchart.com/pages/system.html, 3 pages. Nov. 7, 2013.

Synchart, https://web.archive.org/web/20040614063122/http://www.synchart.com/pages/system.html, 5 pages. Nov. 7, 2013.

Walgreens, https://web.archive.org/web/20010815043713/http://www.walgreens.com/, 1 page. Nov. 5, 2013.

Walgreens, https://web.archive.org/web/20010801143713/http://www.walgreens.com, 1 page. Nov. 5, 2013.

Walgreens Pharmacy, Mar. 3, 2000, http://web.archive.org/web/20000303091027/http://www.walgreens.com/pharmacy/default, 1 page, retrieved from the Internet on Jun. 24, 2013.

Walgreens Historical Highlights, http://www.walgreens.com/marketing/about/press/facts/fact3.jsp, 6 pages. Aug. 13, 2013.

National Committee on VItAL and Health Statistics, Letter to Honorable Michael O. Leavitt, Secretary, U.S. Department of Health and Human Services, http://ncvhs.hhs.gov/050909lt.htm, 11 pages. Sep. 9, 2005.

U.S. Department of Health and Human Services, "A Report Recommendation From the National Committee on Vital and Health Statistics, Personal Health Records and Personal Health Record Systems", 35 pages. Feb. 28, 2006.

Szolovits, Peter, et al., "Guardian Angel: Patient-Centered Health Information Systems", Massachusetts Institute of Technology, http://groups.csail.mit.edu/medg/projects/ga/manifesto/GAtr.html, 43 pages. May 31, 1994.

MyMedicalRecords.com, Inc., Examiner's Report from Australian Patent Application No. 2006202057, 2 pages. Jul. 31, 2007.

mymedicalrecords.com, Inc., PCT/US06/04867, Notification of Transmittal of International Preliminary Examination Report. May 17, 2010.

www.linx.com, Obtained from Internet Archive Wayback Machine (www.archive.org), linxconnect.htm, linxconnect_faq.htm. Jan. 7, 2005.

http://web.archive.org/web/20050909014053/http://www.mbox.com.au, "mBox—Unified Messaging", 1 page. Aug. 11, 2009.

HealthData Management, "Is the Industry Ready to Get Personal", http://www.healthdatamanagement.com/issues/20_4/phr-personal-health-records-consumer . . . , 8 pages. Jan. 29, 2013.

Philip Marshall MD, MPH, WebMD Corporation, "Personal Health Records—An Overview", NCVHS Hearing, 26 pages. Jan. 6, 2005.

Internet Archive of 2005, http://www.personalmd.com, 11 pages. Apr. 24, 2013.

Cohen, Perry, "Managed Care Pharmacy: Leading Pharmaceutical Care Integration Forward", Journal of Managed Care Pharmacy, vol. 3, No. 2, pp. 139-154. Apr. 30, 1997.

Rite Aid News, http://www.riteaid.com/company/news/news_details.jsf?itemNumber=318, 2 pages, retrieved from the Internet on Apr. 2, 2014.

Petition for Inter Partes Review of U.S. Pat. No. 8,301,466, Exhibits 1001-1025. Feb. 13, 2013.

www.biscom.com, Biscom website, faxcom healthcare.htm, fax_facts.htm, mercyhealth.html, ge.htm, stfrancis.html, faxcom_web_client_htm, bpm.htm. Mar. 31, 2005.

Freier, A. et al., "The Secure Sockets Layer (SSL) Protocol Version 3.0", Internet Engineering Task Force (IETF), https://patientsite.bidmc.harvard.edu, pp. 1-67. Aug. 31, 2011.

Rubenstein, Sarah, "Next Step Toward Digitized Health Records", http://online.wsj.com/news/articles/SB111559580025227759 [retrieved from the Internet on Mar. 4, 2014], 4 pages. May 9, 2005.

Sands, Daniel Z. et al., "PatientSite: Patient Centered Communication, Services, and Access to Information", pp. 1-14 Apr. 10, 2014.

Schoenberg, Roy et al., "Internet based repository of medical records that retains patient confidentiality", BMJ, vol. 321, pp. 1199-1203 Nov. 11, 2000.

Wang, Tiffany et al., "Implementing Patient Access to Electronic Health Records Under HIPAA: Lessons Learned", Perspectives in Health Information Management, 1:11, 9 pages. Dec. 31, 2004.

White Paper "HIPAA Security Compliance and F5 Solutions", F5 Networks, Inc., pp. 1-9 Oct. 31, 2007.

Hussain, Daniar, et al., "The Personal Internetworked Notary and Guardian (PING): The Policy Implications of a Patient-Controlled Electronic Medical Record", 80 pages. May 16, 2002.

Maloney, Daniel et al., "My HealtheVet", AMIA 2002 Annual Symposium Proceedings, p. 1215. Dec. 31, 2002.

MedicalRecord.com—Company Information, https://web.archive.org/web/20001216142100/https://medicalrecord.com/companyinfo.asp, archived Dec. 16, 2000, 1 page, retrieved from the Internet on Mar. 30, 2014.

MedicalRecord.com—Health News, https://web.archive.org/web/20001216153100/https://medicalrecord.com/ featureindex.asp, archived Dec. 16, 2000, 1 page, retrieved from the Internet on Mar. 30, 2014.

MedicalRecord.com—Home page, https://web.archive.org/web/200010309062702/https://medicalrecord.com/, archived Mar. 9, 2001, 1 page, retrieved from the Internet on Mar. 30, 2014.

MedicalRecord.com—MedicalRecord.com Introduces Global Records Access and Management Tool System, https://web.archive.org/web/20001217001500/https://medicalrecord.com/press.asp, archived Dec. 17, 2000, 2 pages, retrieved from the Internet on Mar. 30, 2014.

MedicalRecord.com—Privacy https://web.archive.org/web/20001217019000/https://medicalrecord.com/privacy.asp, archived Dec. 17, 2000, 1 page, retrieved from the Internet on Mar. 30, 2014.

MedicalRecord.com—Security, https://web.archive.org/web/20010202201100/https://medicalrecord.com/security.asp, archived Feb. 2, 2001, 1 page, retrieved from the Internet on Mar. 30, 2014.

Wang, Maisie et al., "Personal Health Information Management Systems and its Application in Referral Management", IEEE Transactions on Information Technology in Biomedicine, vol. 8, No. 3, pp. 287-297. Dec. 30, 2004.

MyMedicalRecords.com, Inc., Examiner's Report from Australian Patent Application No. 2006202057, dated Jul. 31, 2007, 2 pages.

www.linxcom.com, Jan. 7, 2005, obtained from Internet Archive Wayback Machine (www.archive.org), linxconnect.htm, linxconnect_faq.htm.

http://web.archive.org/web/20050909014053/http://www.mbox.com.au, "mBox—Unified Messaging", printed off Internet Aug. 11, 2009, 1 page.

MyMedicalRecords.com, Inc., PCT/US06/04867, Notification of Transmittal of International Preliminary Examination Report dated May 17, 2010.

(56) References Cited

OTHER PUBLICATIONS

Kolata, Gina, "Health Plan That Cuts Costs Raises Doctors'Ire", The New York Times, Aug. 11, 2004, http://www.nytimes.com/2004/08/11/health/11model.html?pagewanted=print [retrieved from Internet Dec. 5, 2012], 5 pages.

Mymedicalrecords, Inc., PCT/US2013/20633, "The International Search Report and the Written Opinion of the International Searching Authority, or the Declaration", mail date Mar. 26, 2013.

\* cited by examiner

MyMedicalRecords.com

Instructions to Fax Medical Records

In accordance with 45 C.F.R. // 164.522 and 164.524 (HIPAA Privacy Regulations), I have the right to obtain a copy of my protected health information (PHI) and to have communications sent to me at an alternative location. Please fax a copy of my PHI to my personal, private mailbox at the number below, or email a copy to my personal email address below, after every visit and/or whenever my PHI is updated so I can maintain a copy of my PHI at MyMedicalRecords.com Patient Name _____

DOB _____

Fax To _____
NO COVER SHEET NECESSARY WHEN FAXING

Email To _____

*Fig. 12*

MEDICAL INFORMATION        MyMedicalRecords.com

This card contains protected health information about me. The information on this card and stored at MyMedicalRecords.com may be incomplete and/or may not be current. In the event of an emergency, access www.MyMedicalRecords.com.

MMR Account # _____
Name _____
Address _____
City _____ State _____ Zip _____
Dr. _____ Phone _____
Dr. _____ Phone _____

(Lower portion:)

Insurance _____
Phone _____
Group # _____ ID # _____
Insurance _____
Phone _____
Group # _____ ID # _____
Signature _____ Date _____
I authorize access to my MyMedicalRecords.com account in the event of a Medical Emergency.
MEDICAL INFORMATION

*Fig.13*

In Case of Emergency Please Contact

Name _____

Phone _____ Relationship _____

Secret question or Passcode _____

Name _____

Phone _____ Relationship _____

Secret question or Passcode _____

Current Medications _____

_____

_____

Allergies _____

_____

_____

Blood Type _____

Medical Conditions _____

MY ACCOUNT: JOHN JONES    PRINT MEMBER INFO

EDIT THIS MEMBER

PERSONAL INFORMATION

FIRST NAME : JOHN          MIDDLE NAME :
LAST NAME : JONES          GENDER : MALE
DATE OF BIRTH : 03 / 28 / 2006

ADDRESS 1 : 1234 MAIN STREET
ADDRESS 2 :
CITY : LOS ANGELES         STATE : CA
ZIP : 90024                ZIP + 4 :

PHONE :                    PHONE 2 :
FAX :                      EMAIL : INFO@MMRMAIL.COM

BLOOD TYPE : O+            BLOOD TYPE NOTES :

EMERGENCY PASSWORD

EMERGENCY PASSWORD :       WHAT'S THIS?  EDIT —904
                     —902

INSURANCE POLICIES

|  | CARRIER | GROUP ID | EMPLOYER ID | EMPLOYEE ID |
|---|---|---|---|---|
| MEDICAL : |  |  |  |  |
| MEDICAL 2 : |  |  |  |  |
| DENTAL : |  |  |  |  |

*Fig.16*

| HOME | MY MEDICAL RECORDS | MY CALENDAR | MANAGE PRESCRIPTIONS | MEDICAL PROVIDERS | MY ACCOUNT |
|---|---|---|---|---|---|

FOLDER ADMINISTRATION

WELCOME MMR

YOUR MMR LIFELINE IS:
1-800-555-1212

LOGOUT

ALL FAMILY MEMBERS ▽

- MESSAGE CENTER -

MY ALERTS :
- FAX (0) [VIEW]
- VOICE MAIL (0) [VIEW]
UPCOMING EVENTS (0)

- UPLOAD -

UPLOAD A RECORD

MY FOLDERS

TO CHANGE THE NAMES ASSIGNED TO YOUR MEDICAL RECORD FOLDERS, ENTER THE NEW NAMES BELOW AND CLICK THE SAVE FOLDER NAMES BUTTON.

| | CURRENT NAME | NEW NAME | |
|---|---|---|---|
| FOLDER 1: | EMERGENCY | EMERGENCY | NOT ACCESSIBLE |
| FOLDER 2: | CHRISTENSON | CHRISTENSON | ACCESSIBLE |
| FOLDER 3: | DR. SMITH | DR. SMITH | ACCESSIBLE |
| FOLDER 4: | DR. JONES | DR. JONES | ACCESSIBLE |
| FOLDER 5: | X-RAYS | X-RAYS | ACCESSIBLE |
| FOLDER 6: | EKG | EKG | NOT ACCESSIBLE |
| FOLDER 7: | DR. MILLER - EYES | DR. MILLER - EYES | NOT ACCESSIBLE |
| FOLDER 8: | IMMUNIZATIONS | IMMUNIZATIONS | NOT ACCESSIBLE |
| FOLDER 9: | PROGRESS NOTES | PROGRESS NOTES | NOT ACCESSIBLE |
| FOLDER 10: | FORMS | FORMS | NOT ACCESSIBLE |
| FOLDER 11: | NUTRITIONAL INFO | NUTRITIONAL INFO | NOT ACCESSIBLE |
| FOLDER 12: | MOM 7 DAD | MOM 7 DAD | NOT ACCESSIBLE |
| FOLDER 13: | PERSONAL INVENTORY | PERSONAL INVENTORY | CREATE PASSWORD |
| FOLDER 14: | MEDICAL RECORDS | MEDICAL RECORDS | CREATE PASSWORD |

*Fig.18*

MY MEDICAL RECORDS

ADD A HISTORY RECORD

FAMILY MEMBER : JOHN

HISTORY TYPE : ALLERGY    SHOW IN EMERGENCY

PRESCRIPTION :

DATE : 06/28/05

MEDICAL PROVIDER : SMITH, DARRELL    CREATE NEW

ENTERED : 06/28/05

NOTES :

SAVE    CANCEL

*Fig.19*

EMERGENCY LOGIN

USER ID :
EMERGENCY PASSWORD :
NAME :
ORGANIZATION :
PHONE NUMBER :

SUBMIT

*Fig.22*

| PATIENT INFORMATION | PRESCRIPTIONS | | | |
|---|---|---|---|---|

PRESCRIPTIONS : FOR JOHN BROWN

| NEXT REFILL | DRUG | MEDICAL PROVIDER | NOTES | VIEW |
|---|---|---|---|---|
| 03/28/06 | SINGULAR | SMITH, JOHN | | VIEW |
| 03/28/06 | CARDIZEN | JONES, JIM | | VIEW |

*Fig.25*

EMERGENCY PASSWORD     -922

EMERGENCY PASSWORD : MEDICAL2

EMERGENCY PHYSICIAN ACCESS     -924

CLICK HERE TO UPDATE PHOTOGRAPH TO PRESENT [ ] BROWSE -926
IN THE PHYSICIAN EMERGENCY VIEWER :

*Fig.26*

PREPAID CARD FOR SERVICES RELATED TO PERSONAL HEALTH RECORDS

PRIORITY STATEMENT

The present application claims priority to U.S. Provisional Patent Application No. 61/584,599 filed Jan. 9, 2012, entitled "Prepaid Card for Services Related to Personal Health Records" and U.S. Provisional Patent Application No. 61/600,859, filed Feb. 20, 2012, entitled "Prepaid Card for Services Related to Personal Health Records", both of which are hereby incorporated by reference in their entireties.

FIELD OF THE INVENTION

The present invention relates to the collection, storage, and/or management of online records such as personal health records. More particularly, but not exclusively, the present invention relates to a prepaid card for access to services related to online records such as personal health records.

BACKGROUND OF THE INVENTION

Systems such as those available through MyMedicalRecords.com make it easy for consumers to import medical records from all of their health care providers and otherwise collect, store, and manage records in a convenient location. What is needed is a prepaid card for offering services related to personal health records.

BRIEF SUMMARY OF THE INVENTION

Therefore it is a primary object, feature, or advantage of the present invention to improve upon the state of the art.

It is a further object, feature, or advantage of the present invention to provide a prepaid card which allows for prepayment for services which allow for the collection, storage, and/or management of online records such as personal health records.

It is a still further object, feature, or advantage of the present invention to provide a prepaid card for services which allow for the collection, storage, and/or management of online records such as personal health records so as to market such services to individuals at retail locations such as, but not limited, retail stores, grocery stores, drug stores, hospital gift shops.

It is another object, feature, or advantage of the present invention to provide a prepaid card for services which allow for the collection, storage, and/or management of online records such as personal health records so as to allow such services to be given to others for promotional purposes.

Another object, feature, or advantage of the present invention is to provide a prepaid card for services which allow for the collection, storage, and/or management of online records such as personal health records so as to encourage the purchase of such services by those who wish to gift use of the services to others.

A still further object, feature, or advantage of the present invention is to provide a prepaid card for personal health record-related services which also functions as an emergency card.

Yet another object, feature, or advantage of the present invention is to provide for a prepaid card for personal health record-related services which allows for but does not require the prepaid card to be activated at the point of sale such as by swiping of the prepaid card or scanning of the package.

Another object, feature, or advantage to provide a prepaid card that may be used to activate a new account or extend the life of an existing account.

It is a further object, feature, or advantage of the present invention to facilitate health care personnel's compliance with HIPAA or other legal requirements regarding privacy of medical records.

A still further object, feature, or advantage of the present invention is to provide an individual with meaningful access to their healthcare records thereby allowing the individual to exercise their legal rights with respect to controlling access to their medical records.

Yet another object, feature, or advantage of the present invention is providing individuals with immediate access to healthcare records in emergency situations to assist in providing appropriate care.

A further object, feature, or advantage of the present invention is to provide a convenient and cost effective method for healthcare providers to comply with laws regarding privacy of healthcare records.

A still further object, feature, or advantage of the present invention is to provide a convenient and cost effective method for individuals to request that their healthcare providers provide copies of medical records.

Another object, feature, or advantage of the present invention is to provide a private communications link between healthcare personnel and their patients.

Yet another object, feature, or advantage of the present invention is to provide for placing an individual in control of their medical records and allowing them to selectively provide access to others.

A still further object, feature, or advantage of the present invention is to facilitate storing all of an individual or family's medical records and related information in a single location so that healthcare personnel can be given complete medical information/history when needed or analysis can be performed on the medical records.

Another object, feature, or advantage of the present invention is to provide a means for individuals to create calendars to remind them of the need to refill prescriptions.

Yet another object, feature, or advantage of the present invention is to provide a means for individuals to create calendars to maintain doctor's appointments.

A further object, feature, or advantage of the present invention is to provide reminder messages regarding the need to refill prescriptions or remember doctor's appointments.

A still further object, feature, or advantage of the present invention is to provide a method to store, organize, and annotate medical records and also to customize the storage by giving the user the ability to name the folders in which those records are stored.

Another object, feature, or advantage of the present invention is to give users the ability to upload images, such as x-rays or scans.

It is a further object, feature, or advantage of the present invention to upload multiple files at the same time.

Yet another object, feature, or advantage of the present invention is to give users the ability to forward records via fax to a healthcare provider.

Yet another object, feature, or advantage of the present invention is to give users the ability to electronically forward records to a healthcare provider.

A further object, feature, or advantage of the present invention is to give users the ability to see if there are any possible interactions between prescription drugs they are taking.

A further object, feature, or advantage of the present invention is to provide a means for individuals to store and access not only medical records, but other types of health records including dental records, healthcare records associated with pets, and vital documents, including, without limitation, wills, living wills, a power of attorney, and a healthcare power of attorney.

Yet another object, feature, or advantage of the present invention is to allow for the healthcare provider to quickly and easily, yet securely, communicate records associated with an individual to the individual.

One or more of these and/or other objects, features, or advantages of the present invention will become apparent from the specification and claims that follow. No single embodiment of the present invention need exhibit each and every object, feature, or advantage as the present invention contemplates that different embodiments may achieve different objects, features, or advantages.

According to one aspect of the present invention, a system includes a card comprising (a) a first surface, (b) a second surface opposite the first surface, (c) a promotional code printed on the second surface, and (d) a scratch box on the second surface and overlaying the promotional code. The system further includes a web server configured to receive the promotional code on the card and activate a new user account for collecting, storing, and managing personal health records. The account may be a prepaid account. In addition, an address associated with the web server may be printed on the card. A user identifier area, an emergency password area, and/or an emergency contact area may be present on the first surface or the second surface. The system may further include product packaging for the card. The web server may provide for associating a dedicated phone number, a voice mail box, and fax mail box with the user account, the dedicated phone number assigned to the new user account. The web server may be configured to determine a monetary value associated with the promotional code and apply the monetary value to the new user account.

According to another aspect of the present invention, a method for providing a service facilitating online management of personal health records is provided. The method may include receiving data from a prepaid card at a web server, activating a new user account for the online management of personal health records using the data from the prepaid card, and providing online access to the new user account, wherein the user account provides for the online management of personal health records. The step of activating the new user account may include associating a dedicated phone number with the user account, the dedicated phone number assigned to the new user account during the step of activating. The method may further include determining by the web server a monetary value associated with the prepaid card and crediting the new user account with the monetary value associated with the prepaid card.

According to another aspect of the present invention, a prepaid card for prepaying for access to a web site configured to provide for management of personal health records is provided. The card includes a first surface, a second surface opposite the first surface, a promotional code printed on the second surface, and a scratch box on the second surface and overlaying the promotional code. The promotional code may be associated with a monetary value for the prepaid card on the web site configured to provide for management of personal health care records.

According to another aspect, a method for providing a service facilitating online management of personal health records is provided. The method includes receiving data from a prepaid card at a web server, activating a new user account for the online management of personal health records using the data from the prepaid card, and providing online access to the new user account, wherein the user account provides for the online management of personal health records by providing for collecting records from one or more health care providers and making available the records from the one or more health care providers through the user account.

BRIEF DESCRIPTION OF THE DRAWINGS

FIG. 12 is a pictorial representation of a preferred embodiment of a sticker providing instructions for faxing medical records.

FIGS. 13 and 14 are pictorial representations of a preferred embodiment of a wallet card which can be used according to the present invention.

FIG. 16 illustrates one embodiment of a screen display.

FIG. 18 illustrates one example of a screen display which allows a consumer to select which folders are to be displayed when the emergency password is used to access information.

FIG. 19 illustrates one embodiment of a screen display for displaying medical history items.

FIG. 22 is a screen display which collects basic contact information when an emergency login is made.

FIG. 25 is a screen display illustrating prescription information which can be accessed.

FIG. 26 is a portion of a screen display allowing a user to provide a photograph of the user.

DETAILED DESCRIPTION OF THE PREFERRED EMBODIMENT

Figure 27:
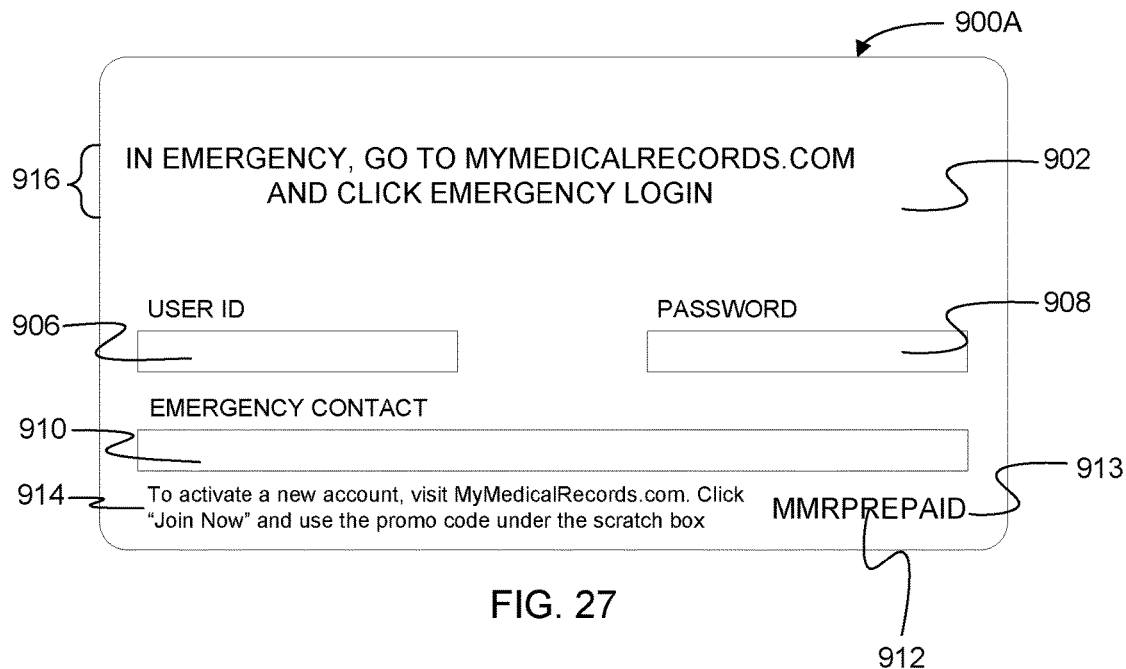
FIG. 27 illustrates a first side of a prepaid card.
Figure 28:
FIG. 28 illustrates a second side of the prepaid card of FIG. 27.

FIG. 27 through FIG. 36 relate to the use of a prepaid card. FIG. 27 illustrates a prepaid card 900A which has a first surface 902. The prepaid card 900A also has a second surface 904 as illustrated in FIG. 28. Returning to FIG. 27, the prepaid card 900A has several different areas on the first surface 902 which may be completed by a cardholder after registration. Alternatively, these different areas may be printed. These areas include a user identification or user id area 906, an emergency password area 908, and an emergency contact area 910.

Also on the prepaid card 900A is registration code or promotional code 913 obscured by a scratch box 912 which overlays the promotional code 913. The promotional code 913 may be a PIN number or other code used to activate the card. There is access information 914 which includes a uniform resource locator (URL) such as a web site address which a cardholder may visit to activate a new account. Alternatively such information may be provided by a QR-code or other type of bar code. There is also emergency access information 916 which includes a URL.

The prepaid card 900A may be used to serve several roles. First, it may be used to provide a physical product which can be sold at retail locations such as retail stores, drug stores, supermarkets, hospitals, hospital gift shops, or other locations. This increases the market for the services being offered, exposing new customers to the services being offered as well as providing a convenient means to gift the services to others. In addition, the prepaid card may also function as an emergency login card. Thus, information for the emergency login features of the service may be placed on the card and the cardholder may carry the card in their wallet or on their person.

Figure 29:
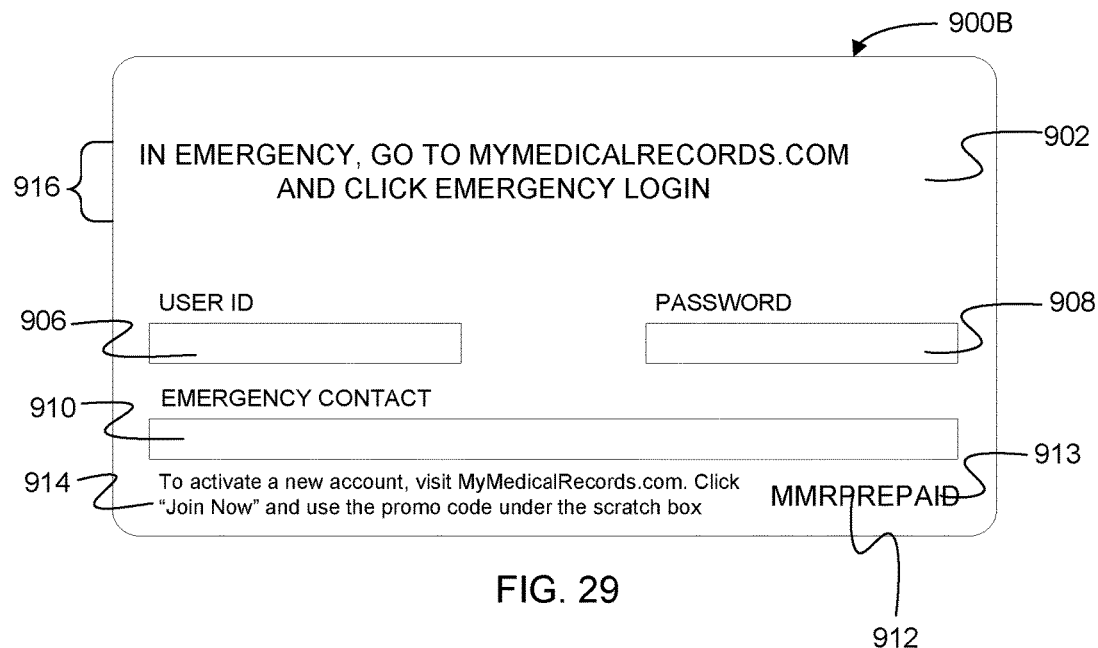
FIG. 29 illustrates a first side of another example of a prepaid card.
Figure 30:
FIG. 30 illustrates a second side of the prepaid card of FIG. 29.
Figure 31:
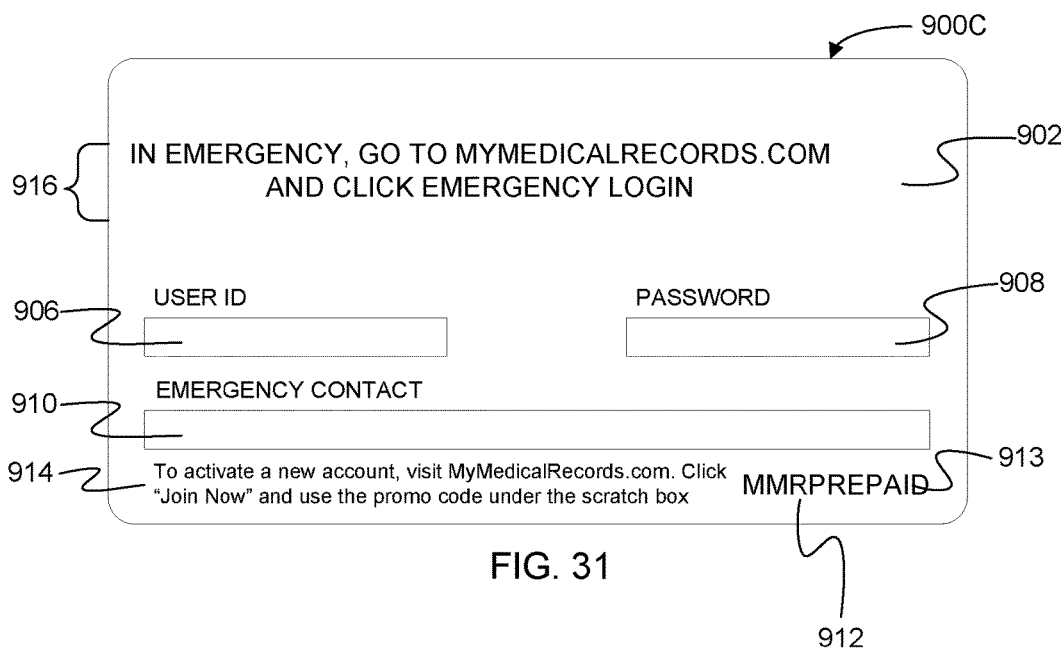
FIG. 31 illustrates a first side of another example of a prepaid card.
Figure 32:
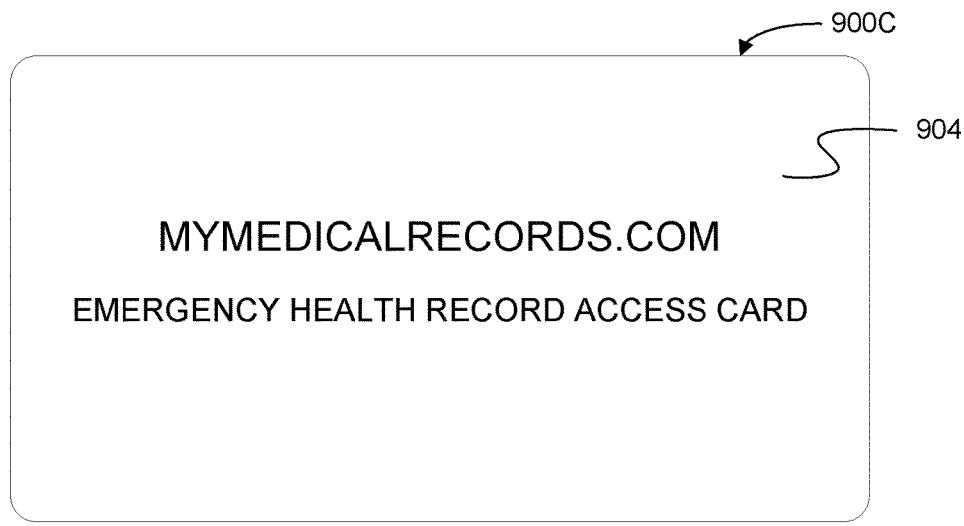
FIG. 32 illustrates a second side of the prepaid card of FIG. 31.

FIG. 29 and FIG. 30 illustrate another example of a prepaid card 900B. FIG. 31 and FIG. 32 illustrate another example of a prepaid card 900C. The card can come with different values. In addition, there may be price incentives associated with the prepaid card such as a price discount for a year of service or an extra month of service or other incentives.

The card may be customized with different logos or images. For example, the card may be customized for different retailers. In addition, the card may be used for promotional purposes.

Figure 33:
FIG. 33 illustrates one side of product packaging for a prepaid card.
Figure 34:
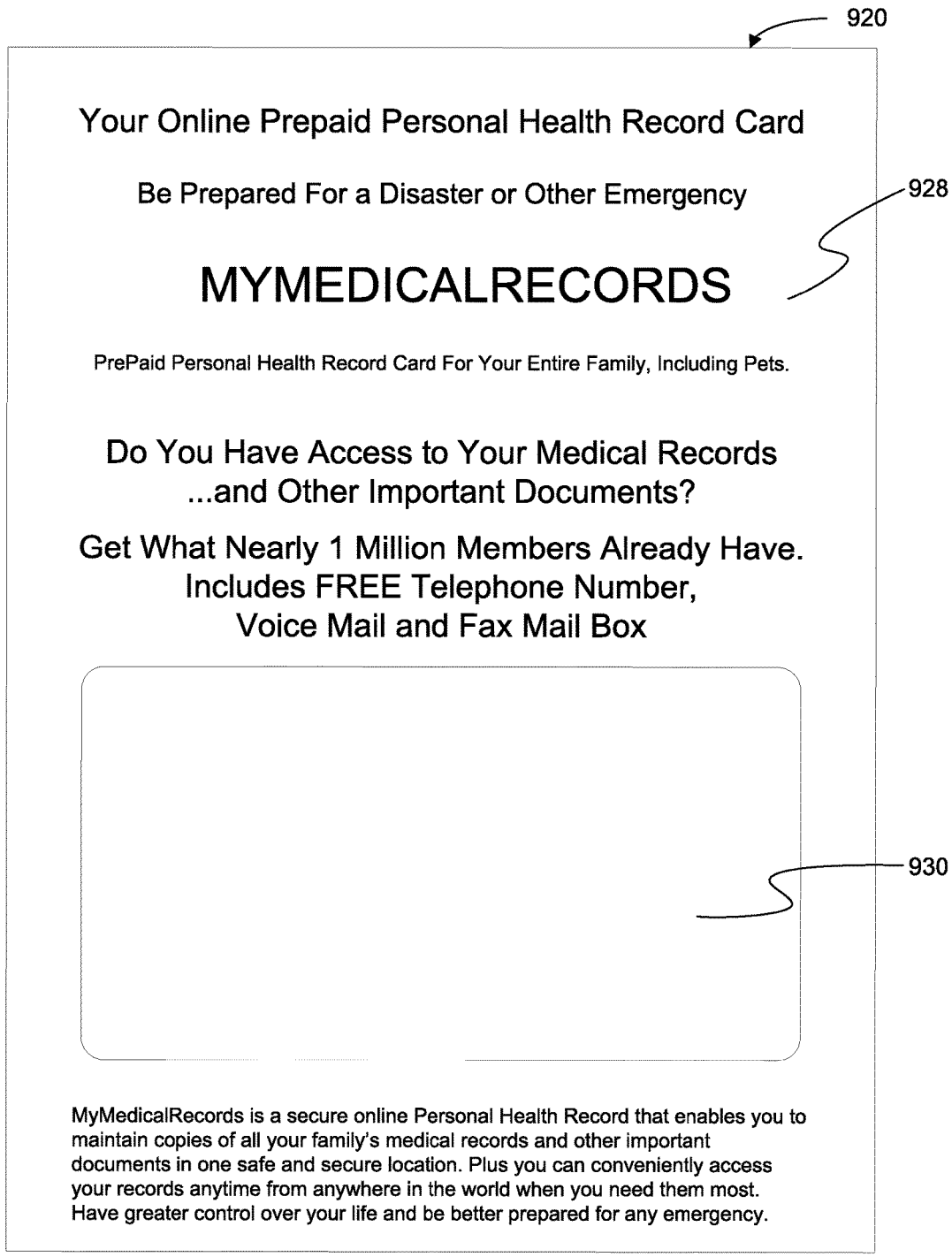
FIG. 34 illustrates an opposite side of the product packaging of FIG. 33.

The card may be packaged in product packaging one example of which is shown in FIG. 33 and FIG. 34. The product packaging 920 includes a back side 921 (FIG. 33) and a front side 928 (FIG. 34). On the back side 921, a web address 932 may be provided. Information about the service 934 may be shown. In addition, instructions 936 for using the prepaid card as an emergency access card may be provided. On the front side 928 a place holder 930 for the prepaid card may be provided.

Figure 35:
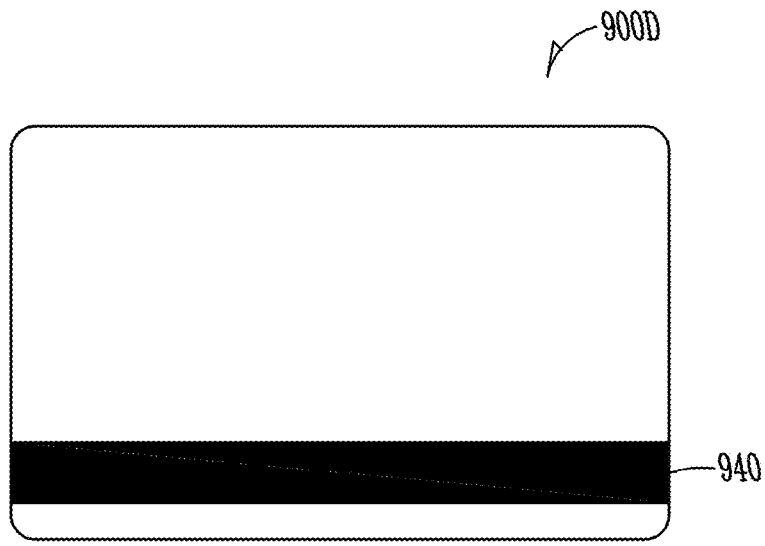
FIG. 35 illustrates an example of a card with a magnetic strip.

The card may also include a magnetic strip (such as in the conventional location) allowing the card to be swiped at the point of sale. Where the card includes a magnetic strip an identifier or other information may be placed on the strip. Thus, the card may be activated at the point of sale by swiping the card. Where the card is activated in this manner, only cards which have been activated at the point of sale could then be used at the web site to create an account. FIG. 35 illustrates one example of a card 900D with a magnetic strip 940.

Figure 36:
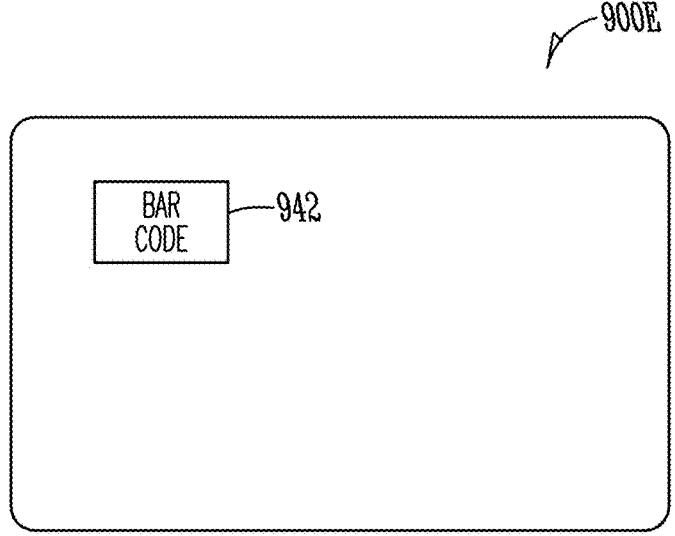
FIG. 36 illustrates an example of a card with a bar code.

Similarly, the packaging may include a bar code which may be scanned, the bar code containing an identifier for the card or other information. The card may be activated at the point of sale by scanning the bar code on the packaging. Where the card is activated in this manner, only cards for which the associated packaging has been activated at the point of sale could then be used at the web site to create an account. FIG. 36 illustrates one example of a card 900E with a bar code 942. It is further contemplated that where one or more bar codes are used they may be in the form of QR-codes or other type of two-dimensional bar codes, or other types of bar codes. Where bar codes are used, the bar codes may be used for identifying web sites, information associated with a cardholder or their account, or other information.

The card may also be used not just to fund a new account associated with a web site, but also to add funds to an existing account or pay for additional services. Thus, the web site can provide for extending the time period for an existing account.

The card may be sold or distributed through retail channels including drug stores, pharmacies, grocery stores, and other retailers, including retailers that sell health-related merchandise. In addition, the card may be distributed by health care providers, insurance companies, banks or financial services companies, or employers as part of any program to increase use of patient portals for health information or to provide a benefit to patients, customers, clients, employees, or others. The card may provide for additional services or functionality based on its use. For example, information on the card, including information stored in a magnetic stripe, bar code, RFID tag, or otherwise may be used for additional purposes such as identifying a cardholder or an account associated with a cardholder, or storing other information associated with a cardholder.

The prepaid card provides access to various services. Following is a description of examples of the types of services that may be provided by the prepaid card. The present invention, however, is not intended to be limited to these examples.

The services provide for a convenient method for individuals to collect, store, and manage their private medical information and to provide private communications between the individual and their healthcare providers. The records can come from a variety of different sources. For example, records may come from the health care provider. Where records come from the health care provider, the present invention contemplates that paper records may be collected from the health care provider by having the records faxed. Similarly, electronic records from the health care provider may be directly communicated.

Figure 1:
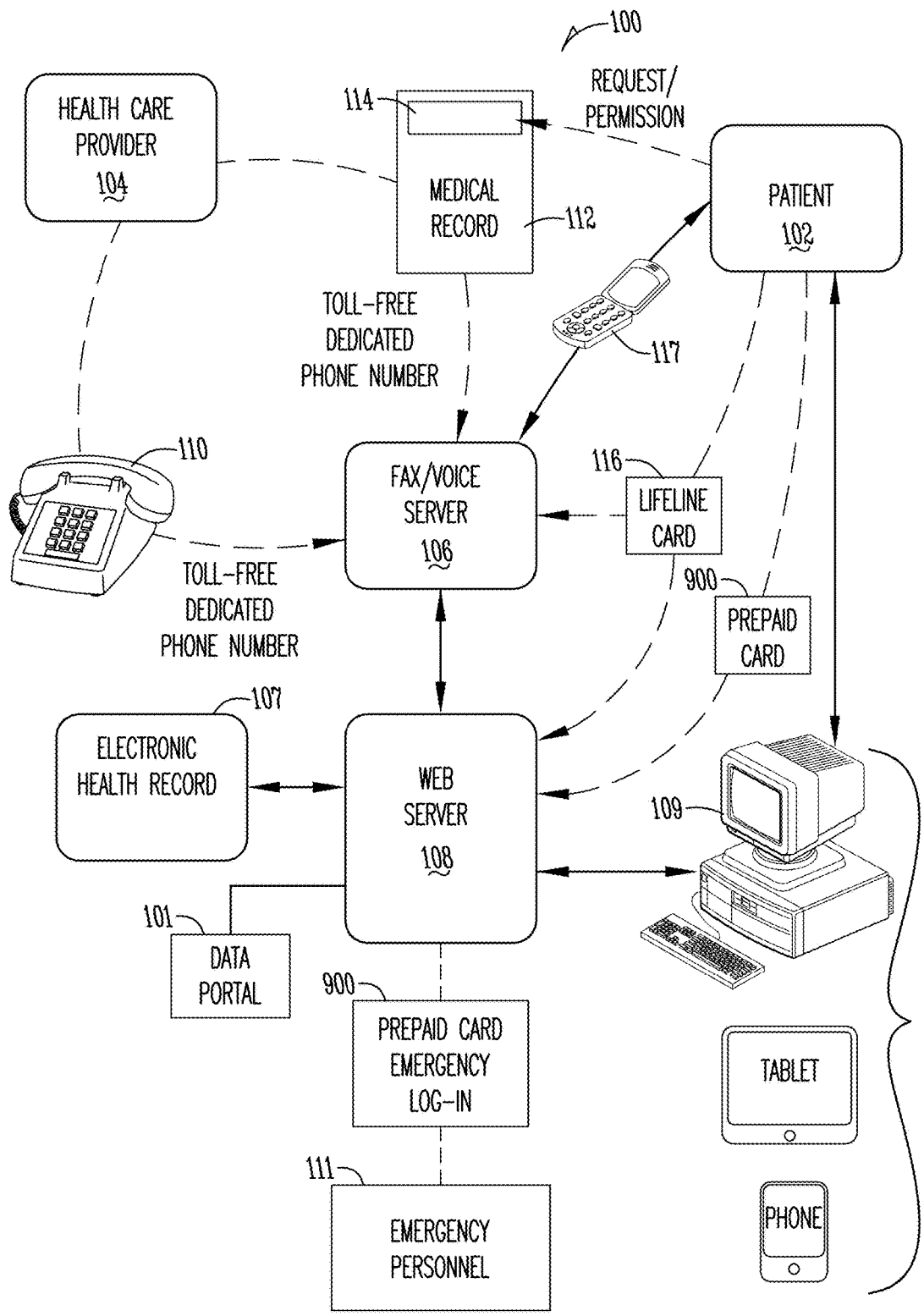
FIG. 1 is diagram illustrating one embodiment of a system of the present invention.

FIG. 1 is a diagram illustrating one embodiment of a system 100 of the present invention. In FIG. 1, a consumer or patient 102 is shown. A healthcare provider 104 is also shown as well as a fax/voice server 106. A web server 108 is operatively connected to the fax/voice server 106. The healthcare provider 104 uses the phone 110 to communicate private voicemail messages through a phone number to the fax/voice server 106. The phone number may be a toll-free number or DID number. In addition, the healthcare provider faxes health or medical records 112 to the fax/voice server 106 using the toll-free dedicated phone number. The medical record 112 (or a folder in which the medical record may be contained) preferably has a sticker 114 present on the medical record 112. The sticker 114 indicates or instructs the healthcare provider 104 or their staff to fax the information to the toll-free dedicated phone number or to otherwise send the information to a destination address. In addition, the sticker 114 provides an indication of clear consent from the patient 102 to the healthcare provider 104 to do so. Thus, it becomes a simple process for a consumer or patient 102 to provide their healthcare provider 104 with instructions to send health records, a simple process for the healthcare provider 104 to obtain permission to fulfill a request for healthcare records, and a simple process for the healthcare provider 104 to do so in a secure and convenient manner.

The web server 108 is operatively connected to the fax/voice server 106 such as over a network or otherwise. A patient 102 or their proxy can communicate directly with the web server 108 through a computing device 109 (which may be, without limitation, a computer, tablet, smart phone, web-enabled device,) or the fax/voice server 106 using a phone 117. The patient 102 can use a LIFELINE card 116 that contains access information to log on to the web server 108 associated with a web site of the present invention, or as a reminder of their toll free dedicated phone number which they can call to access voicemail messages, listen to text-to-speech conversion of emails, or otherwise access information.

The present invention also allows a patient 102 to upload files using a computing device 109 to the web server 108. Multiple files may be uploaded at the same time. In addition, the patient 102 can use the computing device 109 to interact with the web server 108 to specify that a prescription or other personal health record is faxed via the fax/voice server 106 to a healthcare provider 104.

In addition, the system allows electronic health records 107 to be communicated to the web server 108. Thus, for example, a health care provider could send electronic health records directly to the system such as through their Electronic Health Record (EHR) or electronic medical record (EMR) systems.

The prepaid card 900 may be used by a patient 102 to establish a new user account associated with the web site on the web server 108. The web server 108 may be configured to receive the promotional code on the card and activate a new user account for collecting, storing, and managing personal health records.

In addition, the prepaid card 900 may include emergency login information which may be used by emergency personnel 111 to access the web site on the web server 108. Thus, the prepaid card 900 may have multiple functions, both serving as an emergency log-in card as well as funding a user account.

A data portal 101 may also provide data to the web server 108. For example, a service like that available from 4media (Culver City, Calif.) may collect and consolidate data from disparate services. This data may include lab results, prescription information, clinical data, or other types of data. The data portal 101 provides an additional means for accessing data.

Figure 2:
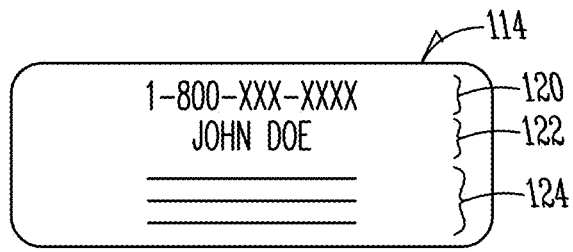
FIG. 2 is a pictorial representation of a sticker authorizing transmissions of records to the user account according to one embodiment of the present invention.

FIG. 2 illustrates one embodiment of a sticker 114 for a patient to give to their healthcare provider to request or instruct their healthcare provider to fax medical records to the toll free dedicated phone number associated with the patient. Although it is preferred that a sticker 114 be used because of the added convenience provided by being able to permanently or semi-permanently attach to a patient file at a healthcare providers office, the present invention contemplates that other types of documents could be used. The sticker 114 includes the LIFELINE phone number 120 which is the toll free dedicated phone number associated with the patient. Note that there is no pin number required which greatly simplifies the process of faxing documents. In addition, the name 122 of the patient is shown. There is also a written request 124 on the sticker 114 that instructs the healthcare provider to fax the records and explicitly gives permission to fax the healthcare record. The language of the written request 124 may vary as necessary to comply with any applicable laws. It should be appreciated that the sticker 114 provides great convenience to both an individual who wants to instruct their healthcare provider to give them access to their medical records as well as to the healthcare provider who can now easily provide the individual with access to their medical records. The present invention further contemplates that medical alert information can also be placed on the sticker 114. The types of medical alert information includes, without limitation, blood type information (i.e. ABO and Rhesus information), allergies to drugs, presence of a pacemaker, diabetes, epilepsy, or other conditions.

FIG. 12 illustrates another embodiment of such a sticker. Note that in FIG. 12, a sticker 800 is shown. The sticker 800 includes instructions to fax or email medical records 802 which serve to exercise a patients rights under 45 C.F.R. §164.522 and 45 C.F.R. §164.524 (HIPAA Privacy Regulations) to obtain a copy of their protected health information (PHI) and to have such communications sent to the patient at an alternative location. In particular, the instructions 802 instruct the healthcare provider to fax a copy of the PHI to a personal, private mailbox at a toll-free or local number after every visit and/or whenever the PHI is updated so that the patient can maintain a copy of their PHI. Alternatively, the instructions 802 provide for instructing the healthcare provider to email the records to specified email address 810.

The sticker 800 includes a region 804 for the patient to print or type their name and a region 806 for the patient to print or type their date of birth. There is also a region 808 for the fax number to which medical records are delivered. Preferably, the number is a toll-free fax or local number assigned to the patient. There is also a region 810 for an email address to which the medical records are to be submitted.

Figure 3A:
FIG. 3A and FIG. 3B illustrate a card with medical record access information according to one embodiment of the present invention.
Figure 3B:
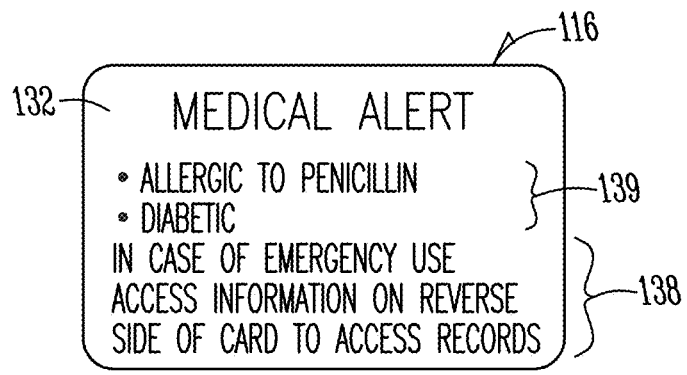

FIG. 3A and FIG. 3B illustrate one embodiment of a LIFELINE card 116. The LIFELINE card has a front side 130 and an opposite back side 132. The card 116 includes the name of the individual 122, a URL for a web site 136 which stores medical records for the individual. In addition there is access information 134 such a username and password. The card 116 also includes the toll free dedicated phone number 120 associated with the individual. On the back side 132 of the card 116 as best shown in FIG. 3B, medical alert information 139 is provided. The medical alert information 139 can include allergies which the individual has, medical conditions such as diabetes or epilepsy, the presence of a pacemaker, or other medical information that may be of great importance in evaluating or treating the individual in the case of a medical emergency. The medical alert information can further include blood type information (i.e. ABO and Rhesus information). Also, instructions 138 are provided on the card 116 to indicate how one could access complete medical records or information about the individual.

The present invention contemplates including the sticker 114 (or other permission/request document) and the LIFELINE card 116 in a welcome kit when an individual or family subscribes or signs-up for the service. In addition, from the web site associated with the service, preferably addition stickers and/or additional cards can be printed and information can be updated as necessary. Stickers and/or cards may be pre-printed with user information (such as name, lifeline number, etc.) from information in a database.

FIGS. 13 and 14 illustrate another embodiment of a wallet card of the present invention. The wallet card 820 includes a first side 822 and an opposite second side 824. As shown in FIG. 13, the first side 822 of the wallet card 820 has a first panel 826 and a second panel 828. The first panel 826 includes identifying information about an individual and emergency instructions 830. The emergency instructions 830 indicate that protected health information can be accessed, in an emergency, at a web site. The second panel 828 of the first side 822 of the wallet card 820 includes insurance information and signature of the patient.

As best shown in FIG. 14, the second side 824 of the wallet card 820 includes emergency contact information, including a secret question or passcode so that the emergency contact person can better verify that there is an emergency, and not a fraudulent notification. The second side 824 of the wallet card 820, also preferably includes information regarding current medications, allergies, blood type, and medical conditions which may be critical to providing appropriate emergency care. A magnetic strip may also be placed on the card which may encode the same or different information.

Figure 4:
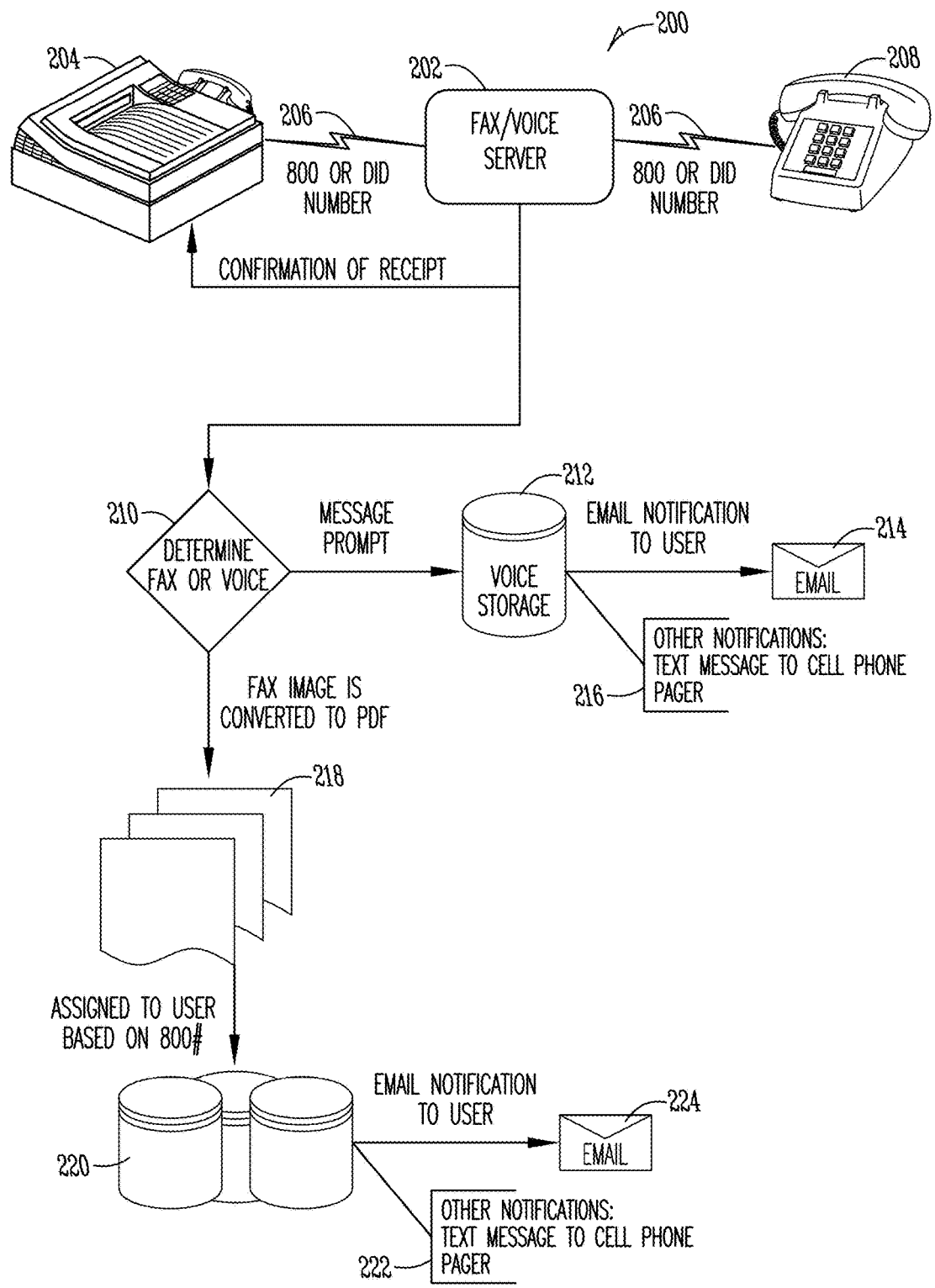
FIG. 4 is a diagram illustrating one embodiment of a system of the present invention.

FIG. 4 illustrates one embodiment of a system of the present invention. As shown in FIG. 4, the system 200 includes a fax/voice server 202. The fax/voice server 202 is accessible by a fax machine 204 or a phone 208 through using a dedicated phone number 206. Preferably, the phone number 206 is toll-free as this increases the accessibility and convenience of the system which is very important. However, the phone number 206 could also be a direct dial phone number. When the fax/voice server 202 receives a call, a determination is made in step 210 as to whether the call is a voice call or a fax call. Where the call is a voice call, an interactive voice response (IVR) system is used to determine who the caller is, the purpose of the call, or other information, and then stores any voicemail message in voice storage 212. The system is adapted to notify the individual that there is a voicemail message through an email notification in step 214 and/or other types of notification in step 216. Other types of notification can include, but are not limited to text messages to a cell phone or pager. Thus, a healthcare provider can call the LIFELINE number 206 and leave a voicemail message for the individual and know that the communication is a private communication. Thus, the healthcare provider can leave private and confidential information, such as the results of a test, or the need to schedule a new appointment, or other information. The individual is alerted to the presence of the voicemail message and can then call-in to the fax/voice server 202 to check messages.

Where documents are faxed, fax images are collected and converted to portable document format (PDF) documents 218. Although, the PDF format is preferred, the present invention contemplates that other types of document conversions can be done as may be appropriate in a particular implementation of the present invention. Based on the dedicated phone number 206 used to send the documents, the faxed documents are assigned to a user account and stored in step 220. The individual is alerted via email that the documents have been sent in step 224. Alternatively, the individual is alerted via text messaging in step 222 that a fax has been sent.

Figure 5A:
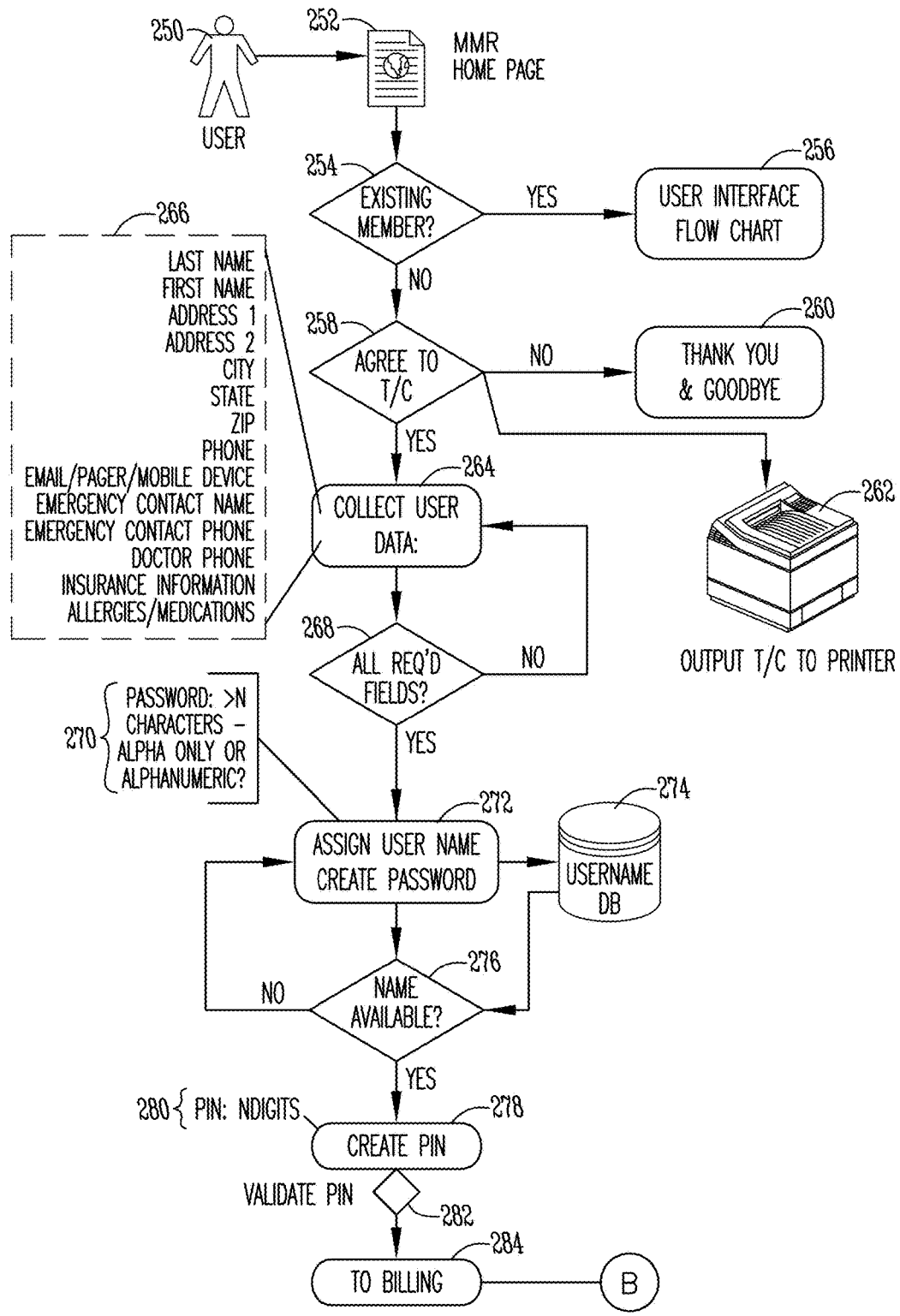
FIG. 5A and FIG. 5B are flow diagrams illustrating an enrollment process according to one embodiment of the present invention.
Figure 5B:
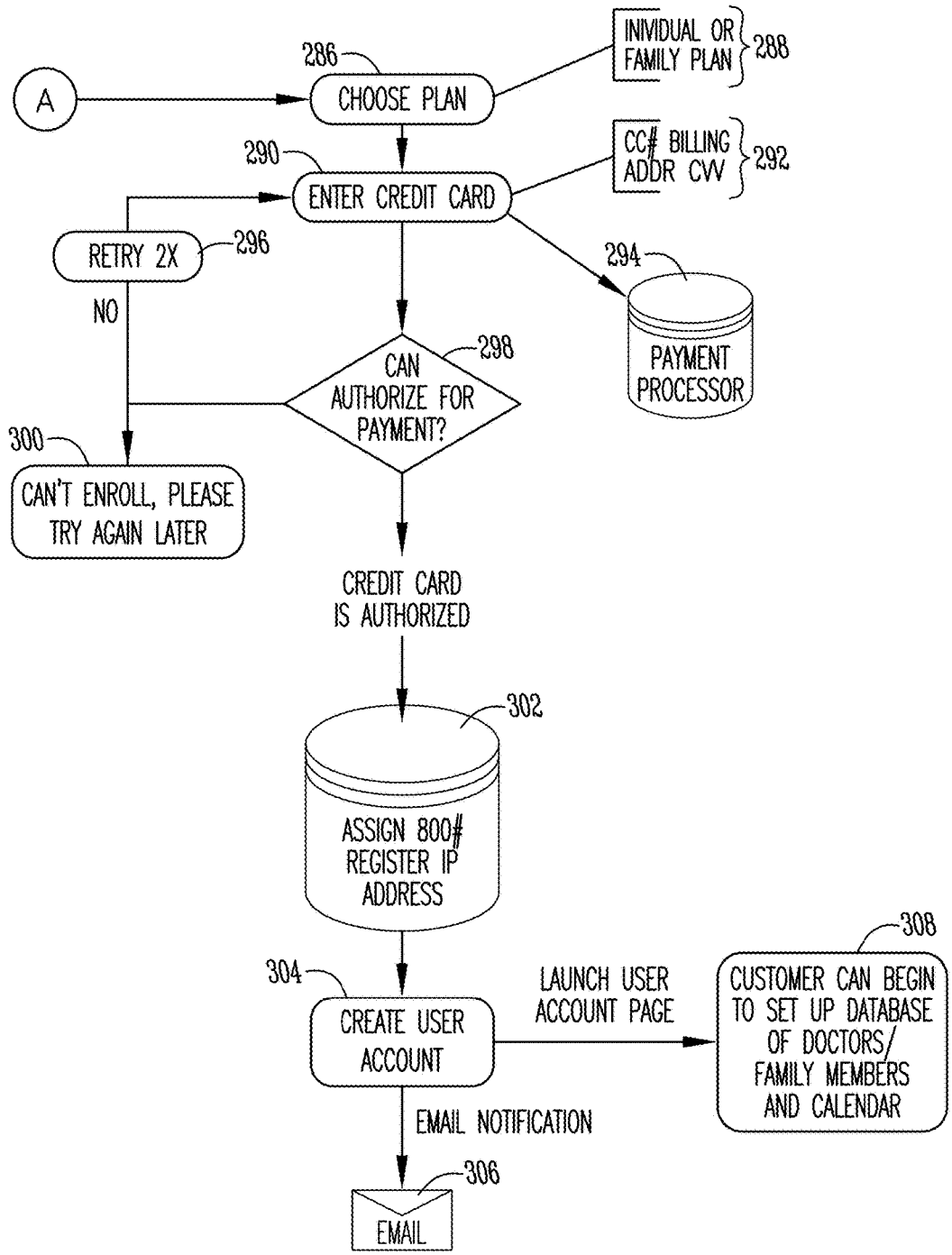
Figure 6:
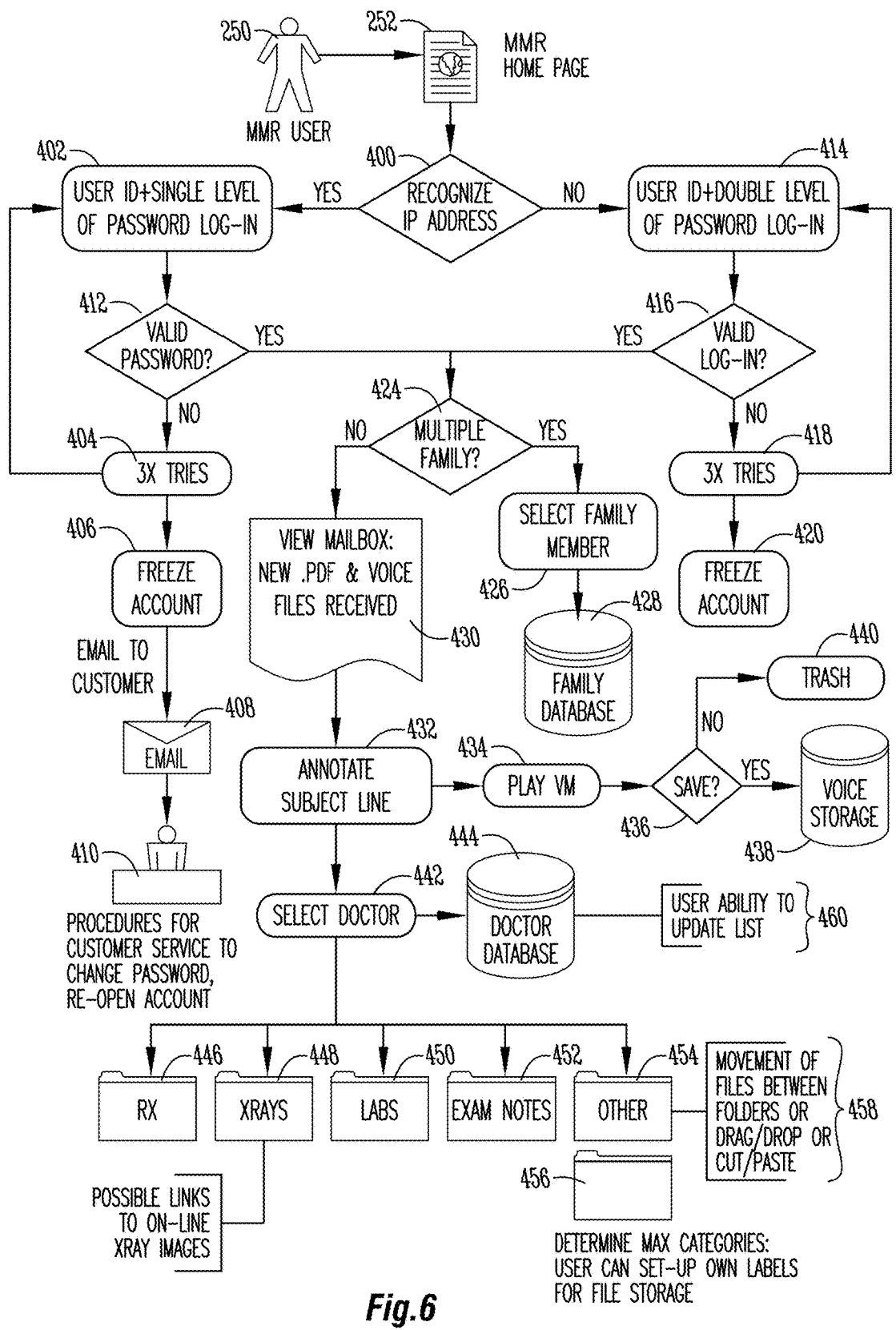
FIG. 6 is a flow diagram for accessing records according to one embodiment of the present invention.

The web site of the present invention provides a convenient location to collect and store healthcare records and provide secure access to the records. It also provides a convenient way to enroll in a service for providing online access to health records. FIGS. 5A and 5B provides one embodiment of an enrollment process In FIG. 5A, a user 250 accesses a home page 252 for a medical records web site. In step 254, a determination is made as to whether the user 250 is an existing member. If the member is, then in step 256 the user is provided access to their user interface as shown in FIG. 6. If not, then in step 258 a determination is made as to whether the user 250 agrees to terms and conditions of service. If not, then in step 260 the user is thanked for their interest but not allowed to continue. The user is also given the option or encouraged to output the terms and conditions to a printer in step 262 so that they can review them closely and maintain a copy for their records if they wish. If in step 258, the user agrees to the terms and conditions of service then in step 264 the system collects user data. User data 266 can include last name, first name, address information, city, state, zip code, phone number, email/pager/mobile device information, emergency contact name, emergency contact phone number, primary care physician phone number, insurance information, allergies and medications, and/or other information. If all fields are received in step 268, then in step 272 the system assigns a user name and password. It is to be understood that the user may also request a particular username and/or set their own password. Where a user selects their own password, then in step 270, a determination is made as to whether the password meets security requirements. For example, there may be a minimum number of characters required, or there must be at least one numeric character, or other requirements. Where the user is allowed to select their own name, in step 274, a username database is searched and in step 276 a determination is made as to whether or not the name is available. If it is, then in 278 the user is permitted to create a personal identification number (PIN). In step 280, a rule such as one requiring a particular number of digits or a particular minimum digits is applied. In step 282 the PIN is validated and the enrollment process proceeds to billing options in step 284. In FIG. 5B, the user is allowed to choose a plan in step 286. The individual could, for example, choose an individual or family plan from the plan options 288. In step 290, the user enters credit card information 292 which may include a credit card number, billing address, and CW number. This information is then submitted to a payment processor 294. In step 298, a determination is made as to whether the credit card information can be authorized for payment. If not, then the number of retries is determined in step 296 and the user is allowed to re-enter their credit card information in step 290. If there have already been two tries to validate credit card information, then in step 300 the individual is told that they can not enroll at this time and should try again later. If payment is authorized in step 298 then in step 302 a dedicated toll free phone number is assigned and an IP address associated with the user is registered. In step 304 a user account is created. In step 306 an email notification confirming registration is sent to the user. In step 308 the user can begin to setup their personal web site such as their database of doctors, family members, calendar, and otherwise configure their web site.

Where a calendar is used, the present invention contemplates that the calendar can be synchronized with an application such as Microsoft Outlook, a calendar program associated with a PDA, or other personal information manager.

Figure 5C:
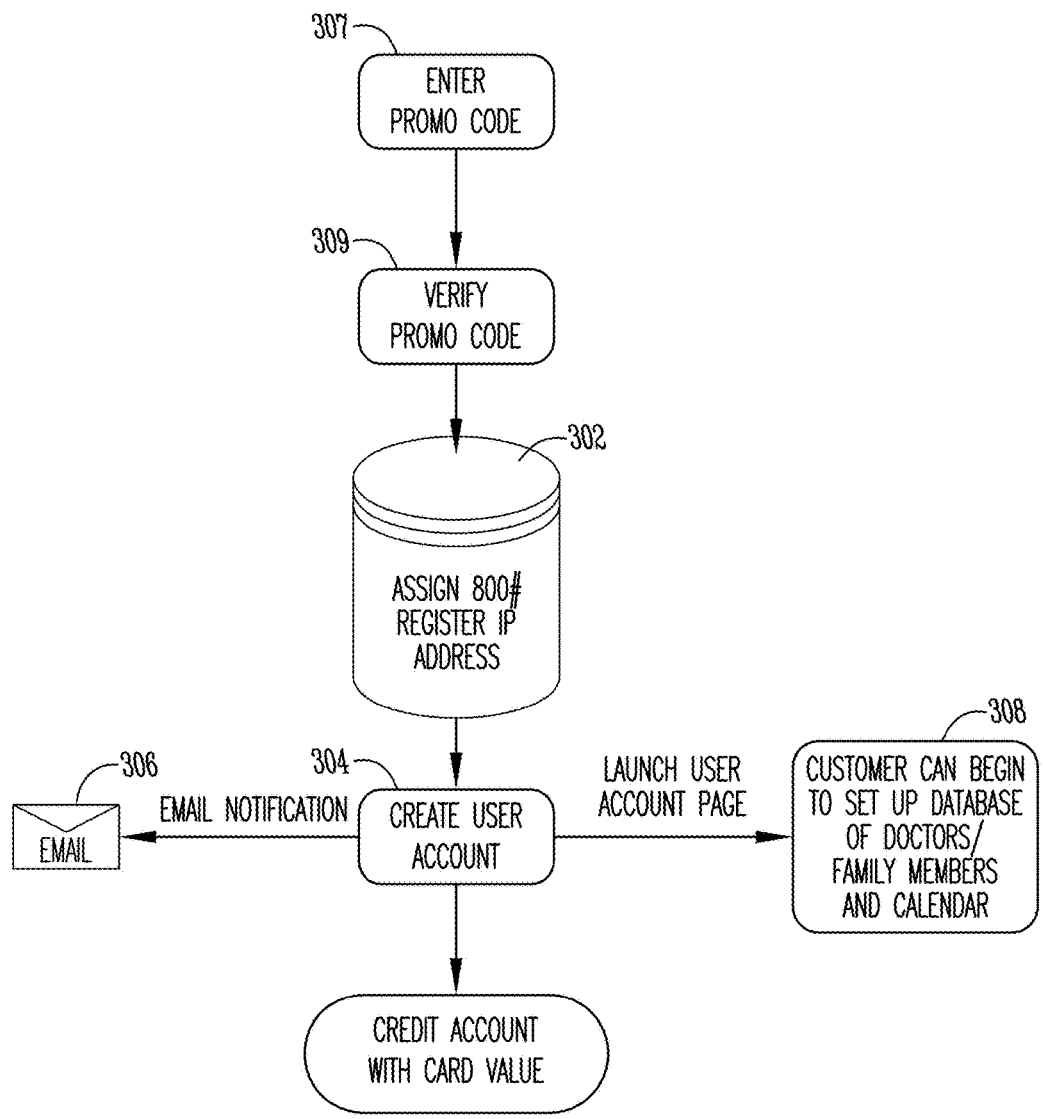
FIG. 5C is a flow diagram illustrating one example of an enrollment process where a prepaid card is used.

FIG. 5C illustrates an alternative enrollment that may be used when a prepaid card is used. In step 307 a promo code on the card is entered. In step 309 the promo code is verified. The promo code or PIN can be verified in various ways. For example, the promo code can be compared against a database of existing promo codes to determine if the promo code is a valid promo code and to determine if the promo code has not been used before. In addition, where activation requires that the card be swiped or other information be collected at the point of sale, the present invention contemplates that as a part of the verification process includes determining whether or not activation has occurred such as by comparing the promo code against a database of promo codes and associated activation information.

In step 302 the normal process of assigning a phone number and registering the IP address is followed. In step 304 the user account is created, an email notification 306 is sent and the user account page is launched. In addition, the user account is credited with the card value in step 311. The card value may be a monetary value associated with the card or a service value. The service value may, for example, be access to the service for a set period of time such as for a particular number of months, days, or years.

After registration, the user can access the user interface of the web site as shown in FIG. 6. The user 250 can access the homepage 252. In step 400, a determination is made as to whether the system recognizes the ip address being used by the user as being associated with the user. If the ip address is not recognized then extra security measures are taken beginning in step 414. In step 414 a username and a double level of password log-in is required. In step 416, if there is a valid log-in, then the process proceeds to step 424. If not, then in step 418, the number of invalid log-in attempts or tries is monitored and if it is three, then in step 420 the account is frozen. Returning to step 400, if the ip address is recognized as being associated with the user, then in step 402 a username and a single level of password log-in is required. In step 412 a determination is made as to whether or not the password is valid. If a valid password, then the process proceeds to step 424. If not, then in step 404 a determination is made as to the number of invalid attempts. After three invalid attempts, in step 406 the account is frozen and in step 408 an email is sent to the individual who may, in step 410, implement procedures to change the password and re-open the account.

Returning to step 424, a determination is made as to whether the account is associated with an individual or a family. If the account is associated with a family, then in step 426, the user can select the family member and access the family database 428. If, in step 424 the account is not a family account, then in step 430 the user can view their mailbox showing new PDF files and voice files. Preferably, these new files include date and time stamps so that the user can see when the files were received.

In step 432, the user is allowed to annotate the messages to better identify the messages in a manner that is convenient for the user. In step 434, the user can play the voicemail messages. In step 436, the user can choose to save the messages to voice storage 438 or to send the message to the trash 440. In step 442, the user can select a doctor to associate with the voicemail messages. For example, the doctor from which the voicemail or imaged document was received. Preferably the doctor is within the doctor database 444. If not, then in step 460, the user can update the doctor database 444 to include the doctor. The user can then organize the voicemail or document according to the user's preference into one or more file folders. Examples of file folders include RX 446, XRAYS 448, LABS 450, EXAM NOTES 452, OTHER 454. The user can make new file folders such as file folder 456 and identify it appropriately. The user interface offers functions 458 such as movement of files between folders, drag and drop, cut and paste, and/or other functions that will assist the user in organizing their records.

Each of the file folders may be protected with one or more additional passwords. Such an implementation is particularly useful in a number of contexts. For example, the use of multiple passwords allows information such as insurance information, financial information, or other proprietary information to be protected differently than the medical records.

Another example of where this extra layer of security can be useful is where a single account is shared by a family consisting of two parents and multiple children. Each parent may have their own folder separately password protected so that the other parent can not access their folder, but still allowing both parents to access the folders for the children.

Figure 7:
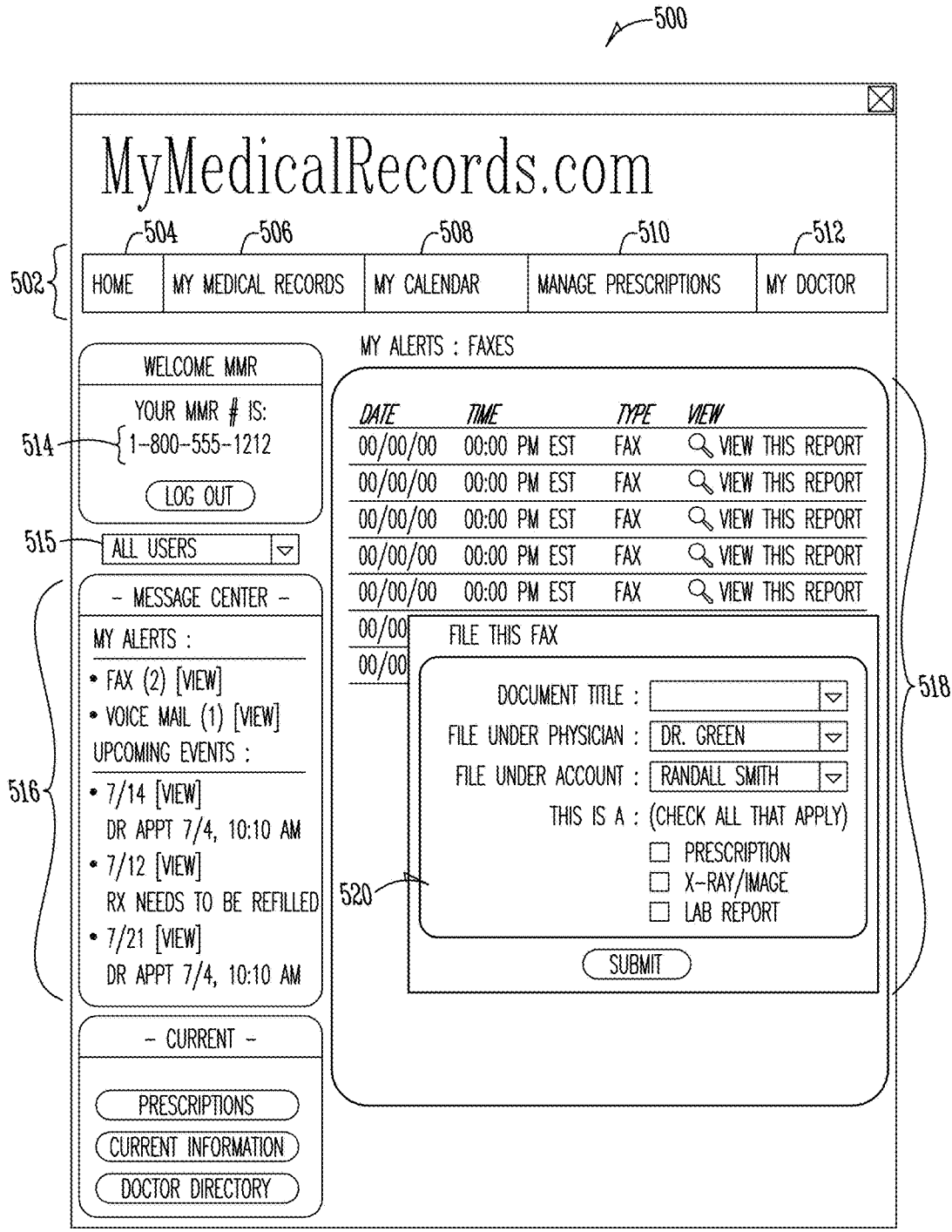
FIG. 7 is a screen display of a web site according to one embodiment of the present invention.

FIG. 7 illustrates one embodiment of a screen display of the present invention. In FIG. 7, the screen display 500 includes a menu bar 502 along the top with different menu items such as "Home" 504, "My Medical Records" 506, "My Calendar" 508, "Manage Prescriptions" 510 and "My Doctor" 512. The screen display 500 also includes a reminder to the individual of their LIFELINE toll free dedicated phone number 514. A message center 516 includes alerts as to recent faxes, voicemails, doctor appointments, prescription refills, or other related events. The user can view the recent faxes 518, and for each fax, can file it using fax filing options 520 which allow the user to give a document title to the fax, associate a physician with the fax, file the fax under a particular account where the account is a family account, and identify the fax as a prescription, x-ray/image, or lab report.

It should also be appreciated that a user need not fax themselves documents. Instead, the user can upload scanned documents or other files in any number of formats.

Figure 8:
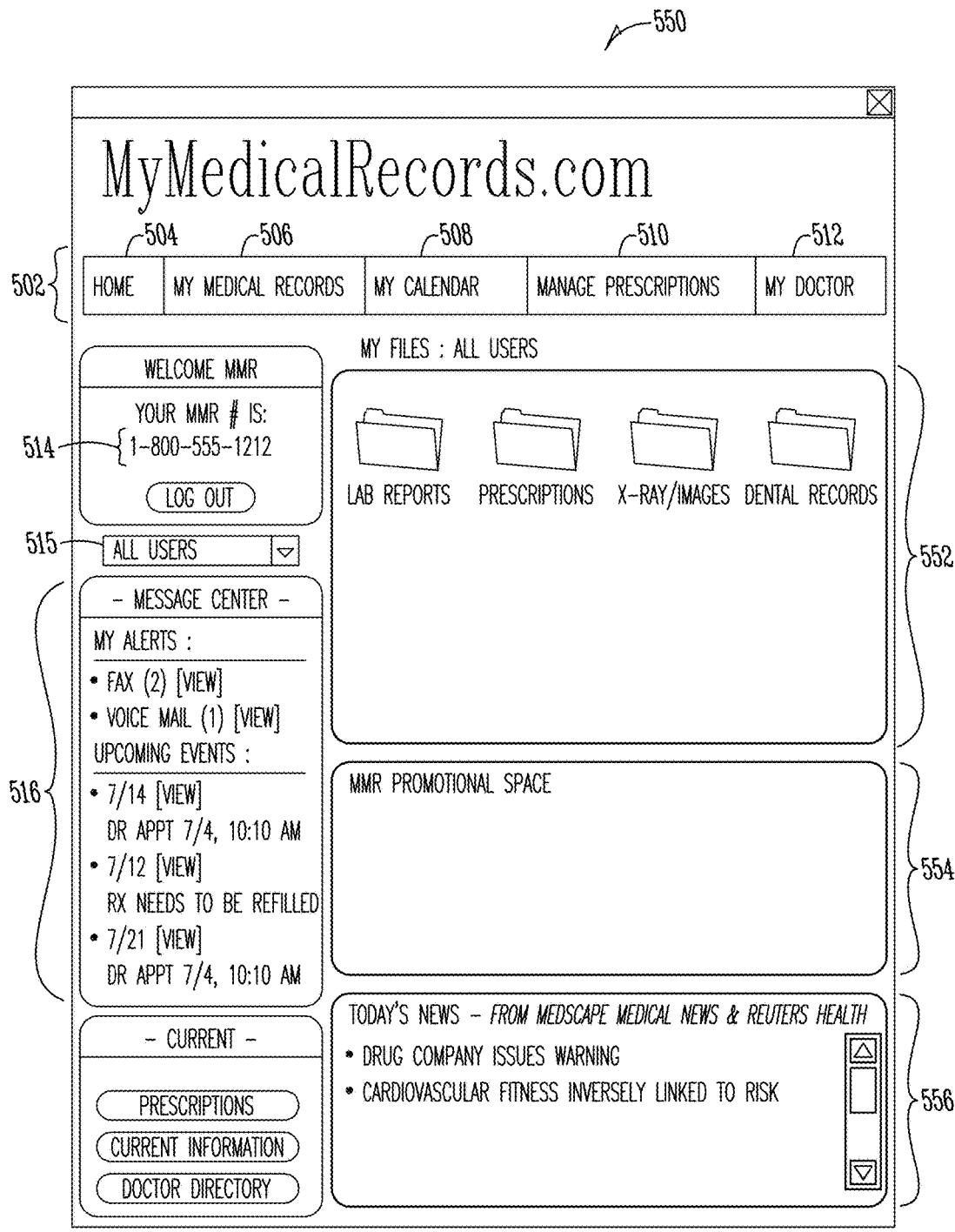
FIG. 8 is another screen display of a web site according to one embodiment of the present invention.

FIG. 8 illustrates another example of a screen display according to one embodiment of the present invention. In FIG. 8, the screen display 550 also includes a files section 552 wherein different folders are shown for storing and organizing information. This allows a user to store records in a manner appropriate for them. In one embodiment, the folders can include separate folders for lab reports, prescriptions, x-ray/images, dental records, lab reports, prescriptions, and all records. As shown in FIG. 8, there is a promotional space 554. The present invention allows for promotional material to be placed in the promotional space 554 that is of potential interest to the user. The promotional information can come from a third party source or advertiser. In additions, news information may be placed in a news information portion 556 of the web page. The news information can include breaking news regarding the medications that the patient is on, health and fitness news, or other news of potential interest or importance to the user.

Figure 9:
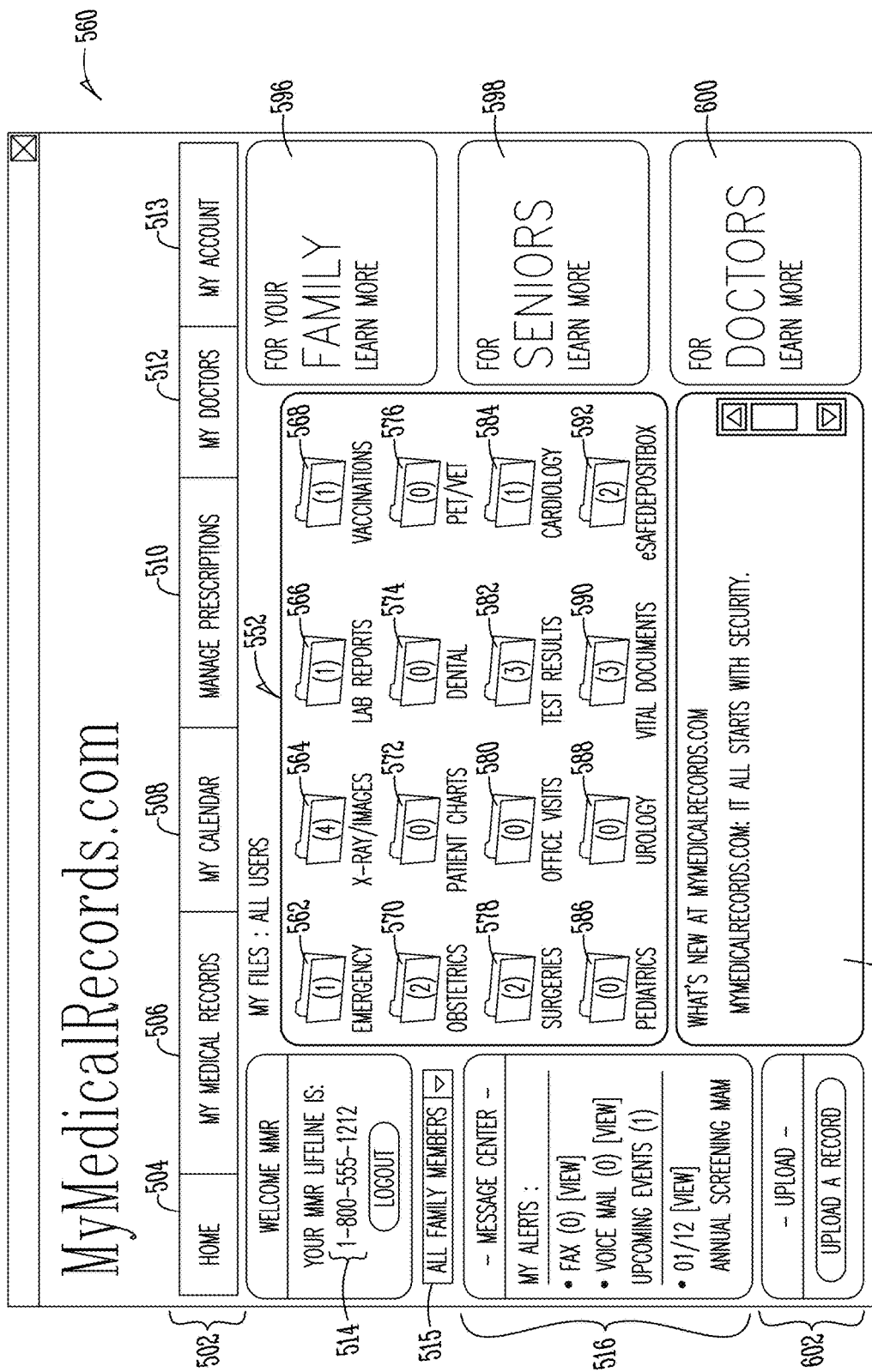
FIG. 9 is a screen display according to one embodiment.

FIG. 9 is another example of a screen display 560 according to one embodiment of the present invention. Note that a MYACCOUNT option 513 is shown near the top of the screen display 560. Also note that a user is allowed to select a family member using the dropdown list box 515. There is also an upload record option 602 provided so that a user may upload files of various types directly to their account.

Shown in the MY FILES portion 552 are a plurality of file folders, including: EMERGENCY folder 562, X-RAY/IMAGES folder 564, LAB REPORTS 566, VACCINATIONS 568, OBSTETRICS 570, PATIENT CHARTS 572, DENTAL 574, PET/VET 576, SURGERIES 578, OFFICE VISITS 580, TEST RESULTS 582, CARDIOLOGY 584, PEDIATRICS 586, UROLOGY 588, VITAL DOCUMENTS 590, eSAFEDEPOSITBOX 592. The various file folders shown provide a convenient method for users to organize their files. Note that each folder indicates how many files are stored within the file folder. It is to be understood that data received through a data portal to a service such as 4media may be placed in an appropriate folder.

A WHAT'S NEW portion 594 allows users to learn about new features or other information. A FAMILY panel 596 can display information or links to information relevant to families. A SENIORS panel 598 can display information or links to information relevant to seniors. A DOCTORS panel 600 can display information or link to information relevant to doctors. Of course, the present invention contemplates that panels 596, 598 and 600 need not be present, and where present can be used to convey other types of information of potential interest to users.

Figure 10:
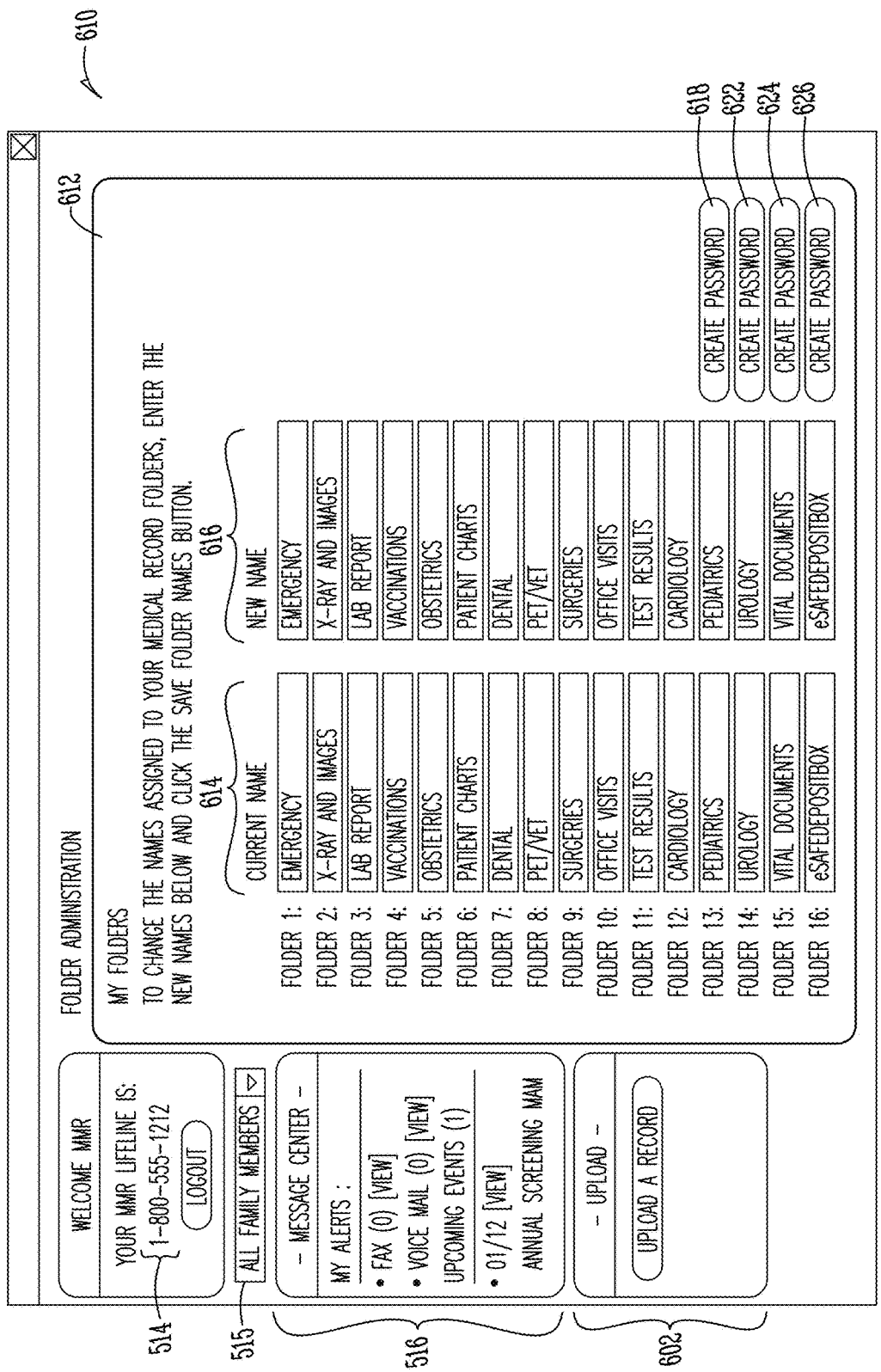
FIG. 10 is a screen display for folder administration according to another embodiment.

FIG. 10 is another example of a screen display according to one embodiment of the present invention. The screen display 610 allows for folder administration. A folder administration portion 612 includes a listing of multiple folders (16 shown) with a column 614 indicating the current name for each folder and a column 616 indicating the new name to be assigned to each folder. In operation a user can change the name of the folders to suit their particular needs. Note that at least a portion of the folders have a password associated with them. This provides an additional layer of security to these files.

Figure 11:
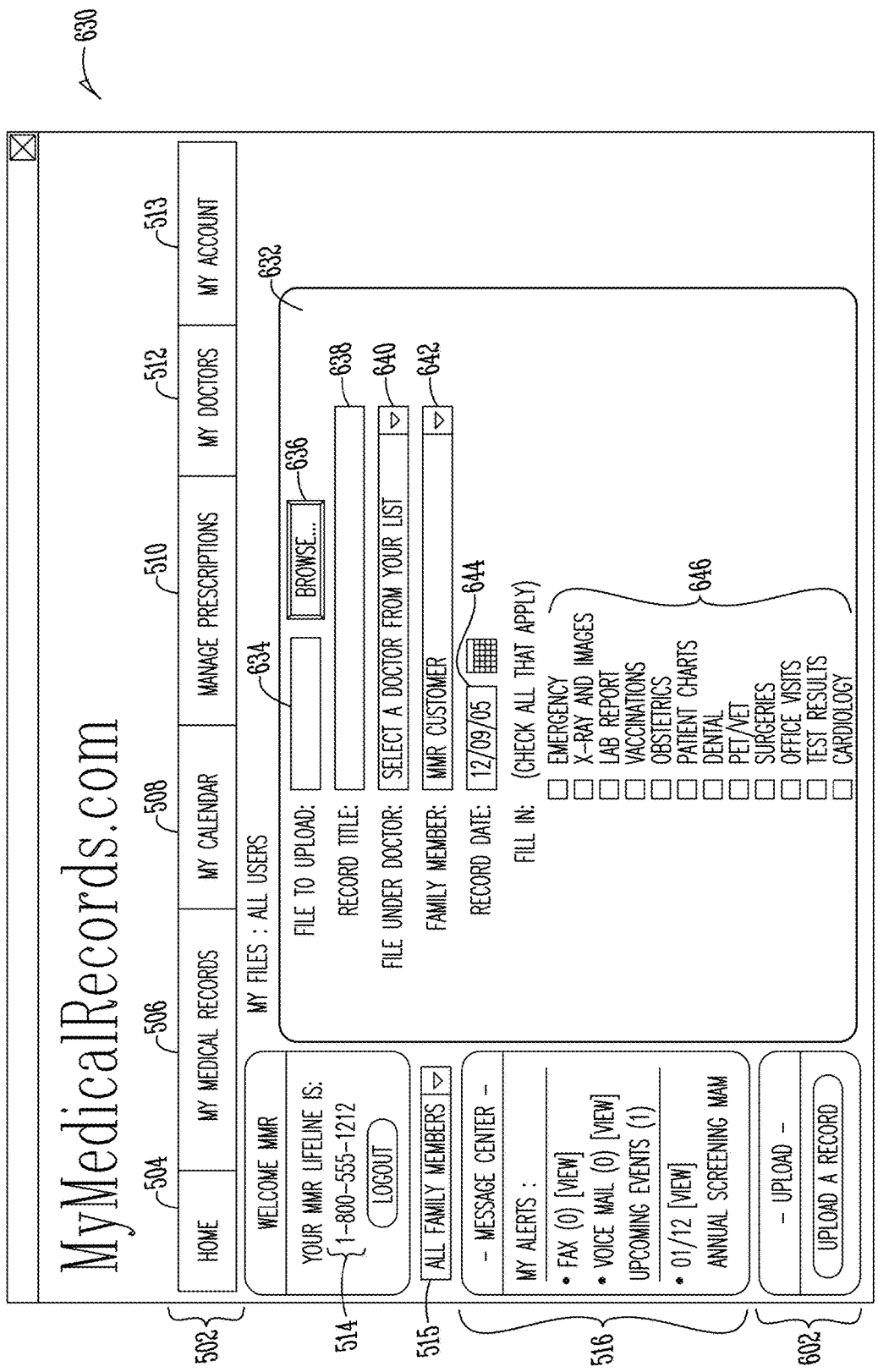
FIG. 11 is a screen display for an uploaded file feature according to another embodiment of the present invention.

FIG. 11 is a screen display for an uploaded file feature according to another embodiment of the present invention. The screen display 630 allows for uploading a medical record 602. The upload a record window 632 allows the user to select a file to be uploaded 634 by browsing 636 to the location of the stored file. For example, if the user has chest x-rays saved in a picture format such as a jpeg, they would be able to browse 636 to the file and upload the file 634 to add to or to make current their present set of medical records. The upload a record window 632 also allows the user to record a title 638 for the file uploaded 634. Additionally, the uploaded a record window 632 allows the user to associate the file uploaded 634 with the appropriate doctor selected from a drop-down list 640. If the account is family or joint type account and allows storing medical records for multiple persons, the user may use the drop-down menu 642 to select the family member 642 to whom this newly uploaded file 634 should be associated with. The upload a record window 632 also allows the user to record a date 644 associated with the newly uploaded file 634. Lastly, the user has the option of selecting the individual folders 646 where he or she would like a copy of the newly uploaded file 634 to be saved. For example, the user may wish to save the chest x-rays in the x-ray and images folder as well as other folders, such as the emergency folder, lab report and/or surgeries folder. The upload a record window 632 allows the user to periodically update their personal medical records with important medical information and associate that information with the appropriate folders. The upload a record window 632 also makes it easy for the user to browse to and save medical files in electronic form in a convenient and organized manner.

In one embodiment, not only is a password required to access the website, but an additional password is required to access such a folder. This feature can be advantageous in a number of different situations. For example, a family may share an account, but each spouse may maintain certain files in confidence from the other. Or where healthcare information is accessed in an emergency (or through fraudulent use of an emergency card), the most private information which is protected with a second level of password protection remains secure. As shown there are buttons 618, 622, 624, 626 for providing a secondary level of password protection.

Figure 15:
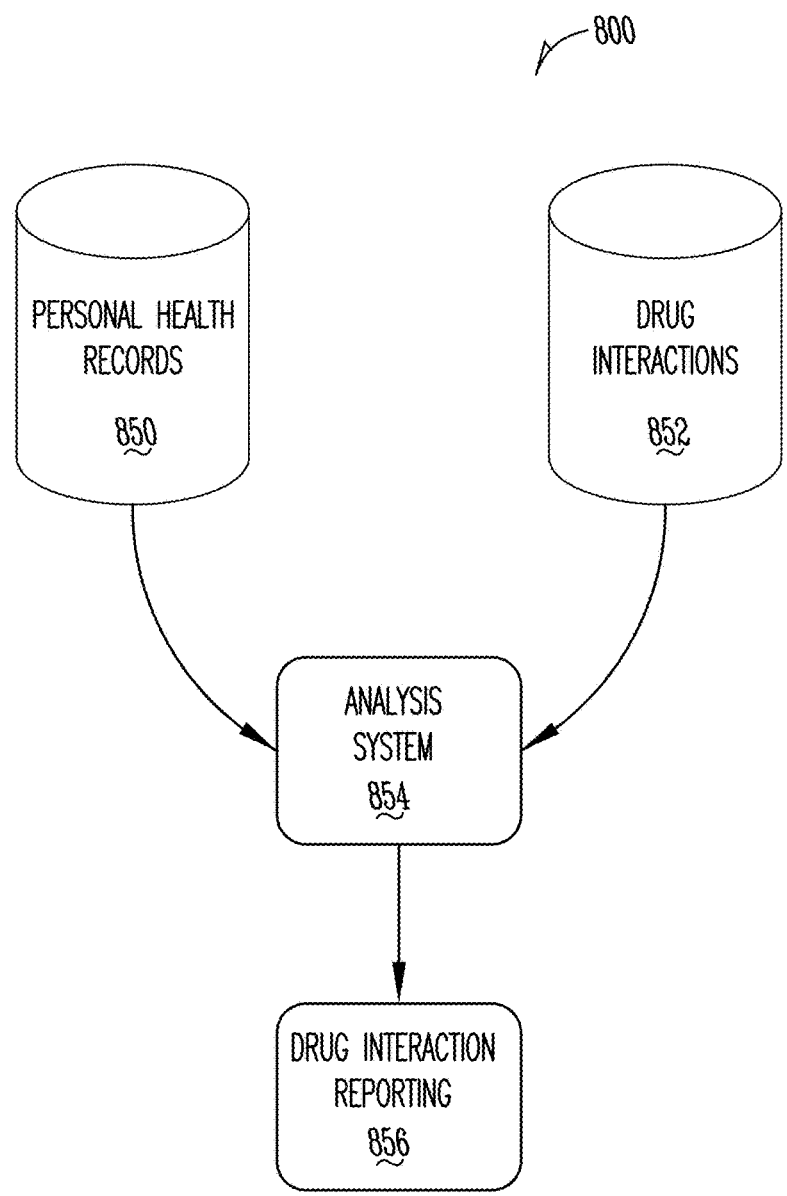
FIG. 15 is diagram illustrating one embodiment of drug interacting reporting and analysis of the present invention.
Figure 17:
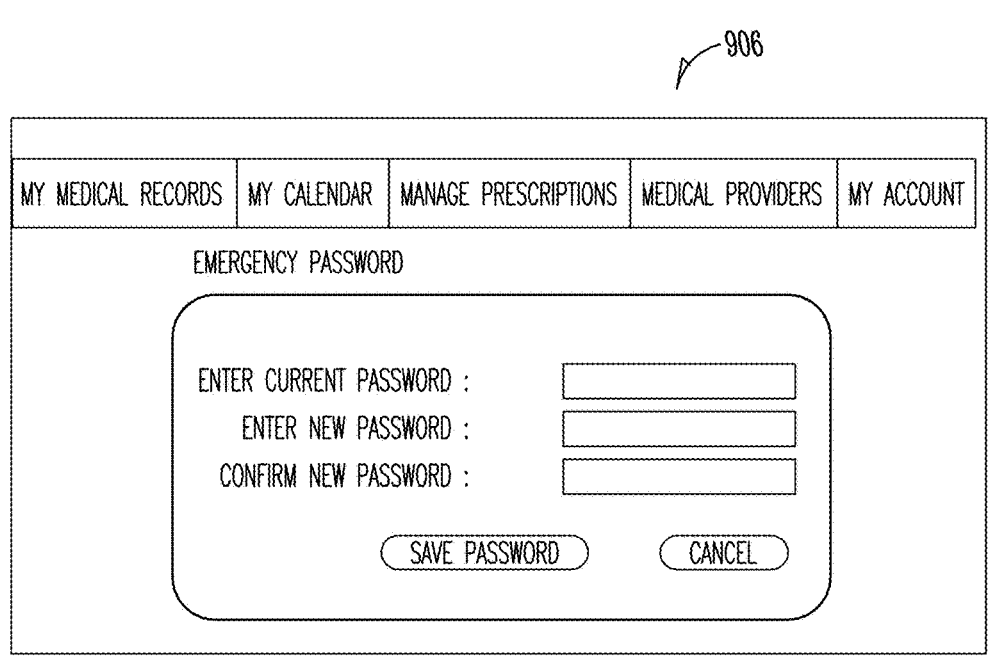
FIG. 17 illustrates one embodiment of a screen display which allows a consumer to set an emergency password.
Figure 20:
FIG. 20 illustrates one embodiment of a screen display for displaying medical history items and which items will be shown in case of emergency.

FIG. 15 illustrates one embodiment of using the health-related information collected to provide additional benefits to a consumer. For example, the present invention allows for a system 800 that includes a personal health records database 850 and a drug interactions database 852 operatively connected to an analysis system 854. The analysis system 854 is operatively connected to a drug interaction reporting component 856. The personal health records 850 includes information regarding which prescription drugs are being taken by the user. The drug interactions database 852 includes information regarding known interactions between different drugs. The analysis system 854 analyzes the prescription drugs taken by the user to determine if there is any known interaction that may be adverse in any way to the user. Based on the results of this analysis, the drug interaction reporting component 856 reports the results to the user, their pharmacist, doctor, or other healthcare provider as appropriate. The present invention contemplates that drug interaction reporting 856 can be reported in different ways to different people based on factors such as user preferences regarding the drug interacting reporting, the severity or certainty of a determined adverse drug interaction, or otherwise. The present invention contemplates that in addition to drug interaction analysis and reporting, other types of analysis and reporting can be performed on the personal health records. One of the advantages of the present invention is that it allows for a convenient method to build and maintain complete and up-to-date health records, thus allowing the personal health records to be analyzed in any number of ways.

FIG. 16 through FIG. 25 illustrate various screenshots of one embodiment of the present invention which provides for providing emergency access to the personal health records associated with a consumer. The emergency password can be assigned to every member of a family. The emergency password—which is different from the normal account log-in—can be used by a doctor or other medical personnel to access critical information in the account in the event of a crisis situation in which a consumer is not able to communicate emergency information. The emergency password preferably is included on a wallet card along with an identifier for the web site to be accessed and instructions for accessing the emergency information.

The emergency password feature allows a consumer to determine which information will be accessible when the emergency password is used. The consumer is in control of their private medical information, even in the event of an emergency. The consumer pre-determines what information they want a doctor, first responder, or other medical personnel to access. This can include what folders are shown, where personal health information is organized into folders. This can also include what items, such as medical history items are shown accessible. Preferably, if an item is not accessible, it is not even shown to preserve maximum privacy for the consumer.

FIG. 16 illustrates a screen display 900 which includes an input box 902 for an emergency password and an "Edit" button 904. After pressing the "Edit" button 904, the screen display 906 of FIG. 17 appears and the consumer can set an emergency password. Next, in FIG. 18, the consumer can select which folders are to be displayed when the emergency password is used to access information. Note that folders are marked as "ACCESSIBLE" or "NOT ACCESSIBLE."

Figure 21:
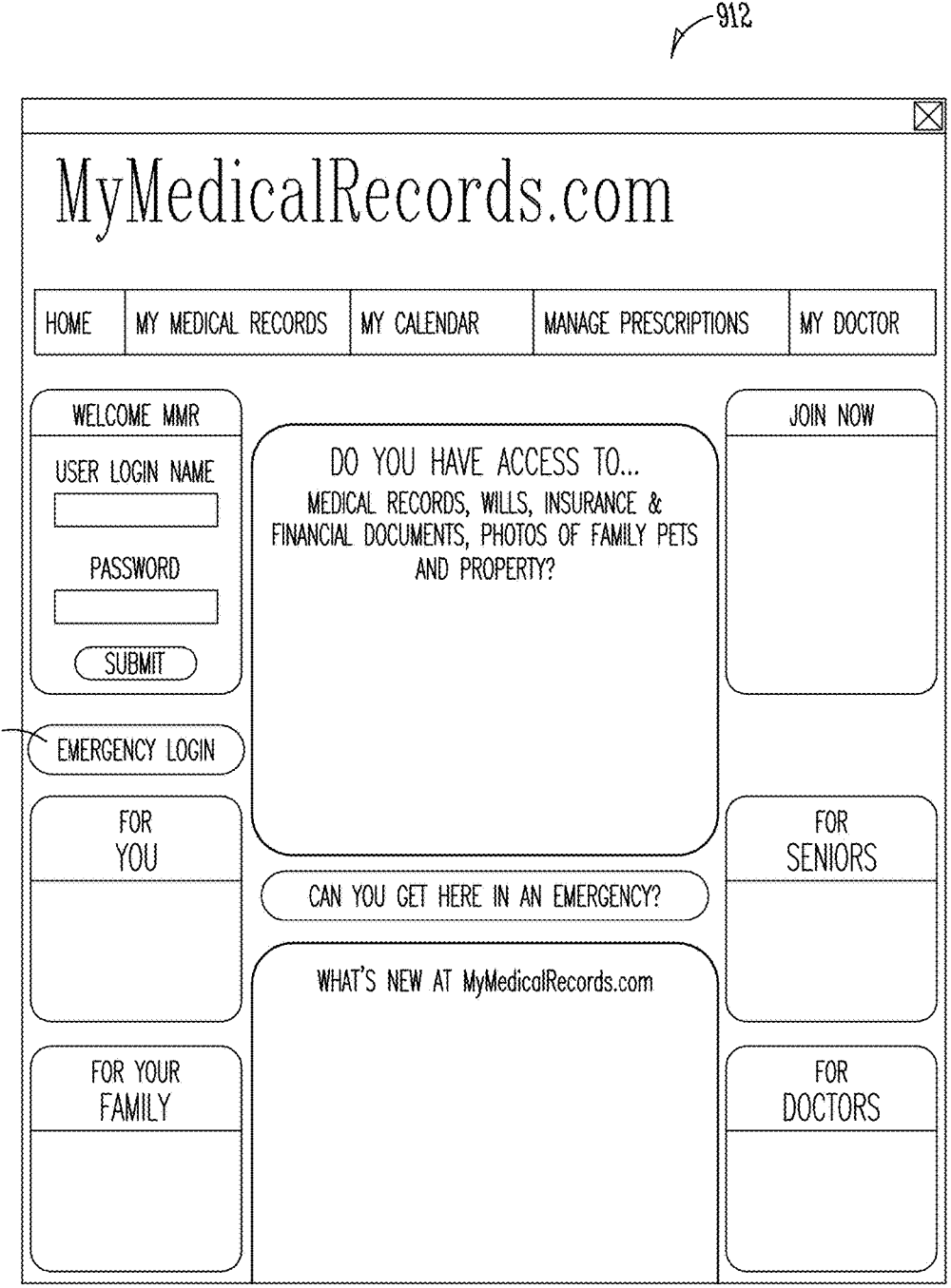
FIG. 21 is a screen display associated with a web site with an emergency login button.

FIG. 19 illustrates medical history items. When new medical history items are added, the consumer can determine whether they want that information shown in case of an emergency. FIG. 21 shows a screen display with medical history items that specifies which items will be shown in case of emergency. An indicator next to each item, such as red cross 910, indicates that the medical history item will be shown in case of emergency.

FIG. 21 is a screen display 912 of a web site which allows a doctor or other health professional to access emergency information in the event of an emergency. Note there is a separate button 914 for an emergency login. The emergency login button 914 is conspicuously placed so that it may quickly be found in case of emergency.

FIG. 22 is a screen display which collects basic contact information when an emergency login is made. The emergency password is validated as a part of the information collection process. The present invention contemplates that this basic information can be used in any number of ways. This information may be stored so that the consumer has a record of who accessed this information. In addition, the present invention contemplates alerting the consumer or the consumer's emergency contacts that an emergency log-in has been made, such as through a phone call, page, or email.

Figure 23:
FIG. 23 is a screen display showing critical information and records provided in case of emergency.
Figure 24:
FIG. 24 is another screen display showing critical information and records provided in case of emergency.

FIG. 23 and FIG. 24 illustrate one embodiment of the most critical information and records which are provided in case of an emergency. Additional information can be accessed from this screen. Note also that in both FIG. 23 and FIG. 24, a photo 920 of the individual may be shown. Having the photo 920 readily available helps first responders or other emergency care providers to verify that they have correctly matched the emergency card with the correct individual, if no one is able to confirm identity of the individual. For example, FIG. 25 illustrates prescription information which can be accessed.

FIG. 26 illustrates a portion of a screen display that allows a user to specify an emergency password 922 as well as upload a photograph or other image file 924. A browse button 926 may be provided to assist the user in identifying the photograph or image file.

Thus, using the emergency password feature, a doctor or other medical or health personnel can quickly see complete information. The emergency password feature, however, does not allow others to add, edit, delete, re-file or otherwise change any of the account information. Thus, the consumer maintains control over their personal health records. In addition, the consumer maintains control over their personal health records by being able to limit access to personal health records by choosing which records are accessible and which records are not.

The prepaid card provides for linking an individual to an account which provides for managing health information and also provides funding for the account through pre-payment, promotional giveaway, or otherwise. The prepaid card further provides the advantage of linking a physical item (the card) to an online service in a manner in which an individual would continue to keep and use the card such as to provide emergency log-in information.

The present invention is not to be limited to the specific disclosure provide herein. The present invention contemplates numerous variations as may be appropriate in a particular context, environment, or situation.

What is claimed is:

1. A system comprising:
a card comprising (a) a first surface, (b) a second surface opposite the first surface, (c) a promotional code printed on the second surface, and (d) a scratch box on the second surface and overlaying the promotional code;
a web server configured to receive the promotional code on the card and activate a new, prepaid user account for collecting, storing, and managing personal health records in response to receiving the promotional code;
wherein the card further comprises an address associated with the web server printed on the card, a user identifier area on the first surface or the second surface of the card for completion by a registered cardholder to specify a user identifier, an emergency password area on the first surface or the second surface of the card for completion by the registered cardholder to specify an emergency password;
wherein the web server is configured to provide emergency personnel with access to a subset of the personal health records in the prepaid user account when the user identifier and the emergency password are used by the emergency personnel to log into the prepaid user account; and
product packaging for the card, the product packaging including a back side and an opposite front side, the product packaging including the address associated with the web server and instructions for using the card as an emergency access card to provide the emergency personnel with access to the subset of the personal health records in the prepaid user account when the user identifier and the emergency password are used by the emergency personnel to log into the prepaid user account;
wherein the product packaging includes a code for scanning at a point of sale.

2. The system of claim 1 wherein the card further comprises an emergency contact area on the first surface or the second surface for completion by the registered cardholder to specify an emergency contact.

3. The system of claim 1 wherein the code is a bar code.

4. The system of claim 3 wherein the web server is further configured to determine if the product packaging associated with the card was previously activated at the point of sale.

5. The system of claim 1 wherein the web server provides for associating a dedicated phone number, a voice mail box, and fax mail box with the user account, the dedicated phone number assigned to the new user account.

6. The system of claim 1 wherein the web server is further configured to determine a monetary value associated with the promotional code and apply the monetary value to the new user account.

7. The system of claim 1 wherein the web server is further configured to determine a service value associated with the promotional code and apply the service value to the new user account, wherein the service value is service for a set time period.

8. The system of claim 1 wherein the web server is further configured to determine if the card has been activated at a point of sale.

9. A prepaid card for prepaying for access to a web site configured to provide for management of personal health care records, the prepaid card comprising:
- a first surface;
- a second surface opposite the first surface;
- a promotional code printed on the second surface;
- a scratch box on the second surface and overlaying the promotional code;
- wherein the promotional code is associated with a monetary value for the prepaid on the web site configured to provide for management of personal health care records, wherein the monetary value is used to activate a new online health records management account or to extend services on an existing online health records management account;
- wherein an address associated with the web site is printed on the care;
- a user identifier area on the first surface or the second surface for completion by a registered cardholder to specify a user identifier;
- an emergency password area on the first surface or the second surface for completion by the registered cardholder to specify an emergency password for use by emergency personnel; and
- an emergency contact area on the first surface or the second surface for completion by the registered cardholder to specify an emergency contact;
- product packaging for the card, the product packaging including a back side and an opposite front side, the product packaging including the address associated with the web server and instructions for using the card as an emergency access card.

10. The prepaid card of claim 9 further comprising magnetic strip on one of the first surface and the second surface.

11. The prepaid card of claim 9 further comprising a bar code on one of the first surface and the second surface.

12. The system of claim 1, wherein the medical records comprise copies of medical documents.

* * * * *